United States Patent
Christensen et al.

(10) Patent No.: US 7,456,001 B2
(45) Date of Patent: Nov. 25, 2008

(54) LIPOXYGENASE

(75) Inventors: Soren Christensen, Jyllinge (DK); Akiko Sugio, Tokyo (JP); Shinobu Takagi, Chiba (JP); Lars Ostergaard, Charlottenlund (DK); Ernst Oliw, Danderyd (SE)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 10/362,776

(22) PCT Filed: Sep. 5, 2001

(86) PCT No.: PCT/DK01/00574

§ 371 (c)(1),
(2), (4) Date: Feb. 20, 2003

(87) PCT Pub. No.: WO02/20730

PCT Pub. Date: Mar. 14, 2002

(65) Prior Publication Data

US 2004/0029225 A1  Feb. 12, 2004

Related U.S. Application Data

(60) Provisional application No. 60/272,604, filed on Mar. 1, 2001.

(30) Foreign Application Priority Data

Sep. 5, 2000 (DK) ................ 2000 01320
Dec. 22, 2000 (SE) .................. 0004790
Feb. 27, 2001 (DK) ................ 2001 00322

(51) Int. Cl.
*C12N 9/02* (2006.01)
*C12N 15/00* (2006.01)
*C12N 1/20* (2006.01)
*C12P 21/04* (2006.01)
*A21D 10/00* (2006.01)
*C11D 3/02* (2006.01)
*C07H 21/04* (2006.01)
*C12Q 1/00* (2006.01)
*C12Q 1/68* (2006.01)

(52) U.S. Cl. .............. 435/189; 435/4; 435/6; 435/69.1; 435/71.1; 435/440; 435/252.3; 435/320.1; 536/23.2; 426/549; 510/108

(58) Field of Classification Search ......... 435/195, 435/189, 4, 6, 252.3, 320.1, 69.1, 71.1, 440, 435/25, 18, 252.2; 536/23.2, 23.74, 23.7
See application file for complete search history.

(56) References Cited

U.S. PATENT DOCUMENTS 5,789,362 A * 8/1998 Baeck et al. ............. 510/226

FOREIGN PATENT DOCUMENTS

| JP | 04094681 | 3/1992 |
| JP | 04094687 | 3/1992 |
| JP | 09065721 | 3/1997 |
| SU | 426640 | 10/1974 |
| SU | 1050627 | 10/1983 |

OTHER PUBLICATIONS

Prigge et al Structure and mechanism of lipoxygenases. Biochimie. Nov. 1997;79(11):629-36. Review.*
A_GenSeq Data Base Acc#AAW93832 Billing-Medel et al Jun. 25, 1999 Human 15S lipoxygenase PS213 protein. Alignment with Seq ID No. 2.*
Branden et al. Introduction to Protein Structure, Garland Publishing Inc., New York, p. 247, 1991.*
Guo et al. Proc Natl Acad Sci USA. Jun. 22, 2004;101(25):9205-10.*
Meinkoth J. and Wahl, G. (1984) Anal. Biochem. 138, 267-284.*
Hornsten et al. Eur. J. biochem. 269:2690-2697 (2002).*
Li D.C. et al, Purification and Charecterization of Lipoxygenase, Mycological Research, vol. 105, Part 2, pp. 190-194, (2001).
Hornsten, Lena et al, Cloning of Linoleate Diol Synthase Reveals, J Biol Chem, vol. 274, pp. 28219-28224, (1999).
Su, Chao et al, Kinetics of Manganese Lipoxygenase , J Biol Chem, vol. 275, pp. 18830-18835, (2000).
Oliw, Ernst et al, Analysis of Novel Hydroperoxides and Other Lipids, Lipids, vol. 33, pp. 843-852, (1998).
Su, Chao et al, Manganese-Lipoxygenase A Novel Model of Abstracts/Prostaglandins and Other Lipid Mediators, vol. 59, pp. 1-235, (1999).
Su, Chao et al, Manganese Lipoxygenase, J Biol Chem, vol. 273, pp. 13072-13079, (1998).

* cited by examiner

*Primary Examiner*—Yong D Pak
(74) *Attorney, Agent, or Firm*—Elias Lambiris

(57) ABSTRACT

The invention provides sequence information of a microbial protein having lipoxy-genase activity and a method of producing the protein by recombinant DNA technology. More specifically, the inventors have isolated a gene encoding a lipoxygenase from *Gaeu-mannomyces graminis*, cloned it into an *E. coli* strain and sequenced it. A comparison shows less than 25% identity to known lipoxygenase sequences, the closest being human 15S li-poxygenase. The inventors have expressed the lipoxygenase recombinantly and found that the recombinant lipoxygenase is glycosylated.

13 Claims, No Drawings

LIPOXYGENASE

CROSS-REFERENCE TO RELATED APPLICATIONS

This application is a 35 U.S.C. 371 national application of PCT/DK01/00574 filed Sep. 5, 2001 (the international application was published under PCT Article 21(2) in English) and claims priority or the benefit under 35 U.S.C. 119 of Danish application nos. PA 2000 01320 and PA 2001 00322 filed Sep. 5, 2000 and Feb. 27, 2001, respectively, and Swedish application no. 0004790-2 filed on Dec. 22, 2000 and U.S. provisional application No. 60/272,604 filed Mar. 1, 2001, the contents of which are fully incorporated herein by reference.

FIELD OF THE INVENTION

The present invention relates to a polynucleotide encoding a lipoxygenase and its use for recombinant production of a lipoxygenase. The invention also relates to a method of obtaining a lipoxygenase by screening a DNA library with specific probes.

BACKGROUND OF THE INVENTION

Lipoxygenase is an enzyme that catalyzes the oxygenation of linoleic acid and produces a hydroperoxide. It is classified in Enzyme Nomenclature as EC 1.13.11.12. The enzyme is widely distributed in plants and animals. Encoding genes have been isolated from various sources, and the sequences have been published. Thus, GENESEQP W93832 and Genbank U78294 give the sequence of human 15S lipoxygenase.

Microbial lipoxygenases are known from a yeast *Saccharomyces cerevisiae*, a thermophilic actinomycete *Thermoactinomyces vulgaris*, from fungus *Fusarium oxysporum*, *Fusarium proliferatum* and *Gaeumannomyces graminis* (Su and Oliw, J. Biological Chemistry, 273 (21), 13072-13079 (1998)). No isolated gene encoding a microbial lipoxygenase has been described.

The prior art describes various uses of lipoxygenase, e.g. as a food additive to bread dough or noodles.

SUMMARY OF THE INVENTION

Here we for the first time provide sequence information of a microbial protein having lipoxygenase activity and a method of producing the protein in industrial scale. More specifically, the inventors have isolated a gene encoding a lipoxygenase from *Gaeumannomyces graminis*, cloned it into an *E. coli* strain and sequenced it. The genome of *G. graminis* contains approximately 60% of the G and C nucleotides, which made this work very difficult. A comparison shows less than 25% identity to known lipoxygenase sequences, the closest being human 15S lipoxygenase. The inventors have expressed the lipoxygenase recombinantly.

Accordingly, the invention provides a polypeptide having lipoxygenase enzyme activity which:

a) has an amino acid sequence which has at least 50% identity with the mature polypeptide of SEQ ID NO: 2 or 23;

b) is encoded by a nucleic acid sequence which hybridizes at 55° C. with a complementary strand of the nucleic acid sequence encoding the mature polypeptide of SEQ ID NO: 1 or a subsequence thereof having at least 100 nucleotides;

c) has an amino acid sequence which can be obtained from the mature poly-peptide of SEQ ID NO: 2 or 23 by substitution, deletion, and/or insertion of one or more amino acids; or d) is encoded by the lipoxygenase-encoding part of the DNA sequence cloned into a plasmid present in *Escherichia coli* deposit number DSM 13586.

The invention also provides a polynucleotide which comprises:

a) the partial DNA sequence encoding a mature lipoxygenase cloned into a plasmid present in *Escherichia coli* DSM 13586, b) the partial DNA sequence encoding a mature lipoxygenase shown in SEQ ID NO: 2 or 23, c) an analogue of the sequence defined in a) or b) which encodes a lipoxygenase and i) has at least 50% identity with said DNA sequence, or ii) hybridizes at low stringency with a complementary strand of said DNA sequence or a subsequence thereof having at least 100 nucleotides, iii) is an allelic variant thereof, or d) a complementary strand of a), b) or c).

Other aspects of the invention provide a nucleic acid construct comprising the polynucleotide, a recombinant expression vector comprising the nucleic acid construct, and a recombinant host cell transformed with the nucleic acid construct. The invention also provides a recombinant method of producing the lipoxygenase, an oligonucleotide probe based on SEQ ID NO: 2 or 23 and a method of obtaining a lipoxygenase by screening a eukaryotic DNA library using the probe based on SEQ ID NO: 2.

Further, the invention provides a dough composition comprising a manganese lipoxygenase and a method for preparing a dough or a baked product made from dough, comprising adding a manganese lipoxygenase to the dough. The invention also provides a method of oxygenating a substrate selected from the group consisting of linolenic acid, arachidonic acid, linoleyl alcohol and a linoleic acid ester comprising contacting the substrate in the presence of oxygen with a manganese lipoxygenase. Finally, the invention provides a detergent composition comprising a manganese lipoxygenase and a surfactant.

DETAILED DESCRIPTION OF THE INVENTION

Genomic DNA Source

DNA encoding the lipoxygenase (LOX) may be derived from fungi, particularly *Ascomycota*, more particularly *Ascomycota incertae sedis* e.g. *Magnaporthaceae*, such as *Gaeumannomyces*, or anamorphic *Magnaporthaceae* such as *Pyricularia*, or alternatively anamorphic *Ascomycota* such as *Geotrichum*. An example is *G. graminis*, e.g. *G. graminis* var. *graminis*, *G. graminis* var. *avenae* or *G. graminis* var. *tritici*, particularly the strain *G. graminis* var. *graminis* CBS 903.73, *G. graminis* var. *avenae* CBS 870.73 or *G. graminis* var. *tritici* CBS 905.73. The CBS strains are commercially available from Centraalbureau voor Schimmelcultures, Baarn, the Netherlands.

The inventors obtained two LOX-encoding DNA sequences from strains of *Gaeumannomyces graminis* and found that they have the sequences shown in SEQ ID NO: 1 and 22. They inserted a LOX-encoding gene into a strain of *Escherichia coli* and deposited it as *E. coli* DSM 13586 on 5 Jul. 2000 under the terms of the Budapest Treaty with the DSMZ—Deutsche Sammlung von Microorganismen und Zellkulturen GmbH, Mascheroder Weg 1b, D-38124 Braunschweig DE, Germany. The deposit was made by Novo Nordisk A/S and was later assigned to Novozymes A/S.

Lipoxygenase

The lipoxygenase of the invention is a manganese lipoxygenase, i.e. it has lipoxygenase activity (EC 1.13.11.12) with manganese in the prosthetic group. It is glycosylated and may have a molecular weight in the range 90-110 kDa, particularly 95-105 kDa. It is thermostable with a temperature optimum of 65-90° C., particularly 75-85° C. The lipoxygenase is stable against LAS (linear alkyl-benzene sulfonate) up to 400 ppm at pH 10. Mn-Lipoxygenase is enzymatically active between pH 5-12 with a broad optimum at pH 6-8.

A recombinant lipoxygenase may have a higher glycosylation and a higher thermostability. The recombinant lipoxygenase may have a molecular weight in the range 90-110 kDa, particularly 95-105 kDa. It may have a temperature optimum of 65-90° C., particularly 75-85° C.

Recombinant Expression Vector

The expression vector of the invention typically includes control sequences encoding a promoter, operator, ribosome binding site, translation initiation signal, and, optionally, a selectable marker, a transcription terminator, a repressor gene or various activator genes. The vector may be an autonomously replicating vector, or it may be integrated into the host cell genome.

Production by Cultivation of Transformant

The lipoxygenase of the invention may be produced by transforming a suitable host cell with a DNA sequence encoding the lipoxygenase, cultivating the transformed organism under conditions permitting the production of the enzyme, and recovering the enzyme from the culture.

The host organism may be a eukaryotic cell, in particular a fungal cell, such as a yeast cell or a filamentous fungal cell, e.g. a strain of *Aspergillus, Fusarium, Trichoderma* or *Saccharomyces*, particularly *A. niger, A. oryzae, F. graminearum, F. sambucinum, F. cerealis* or *S. cerevisiae*. The production of the lipoxygenase in such host organisms may be done by the general methods described in EP 238,023 (Novo Nordisk), WO 96/00787 (Novo Nordisk) or EP 244,234 (Alko).

Nucleotide Probe

A nucleotide probe may be designed on the basis of the DNA sequence of SEQ ID NO: 1 or the polypeptide sequence of SEQ ID NO: 2, particularly the mature peptide part. The probe may be used in screening for LOX-encoding DNA as described below.

A synthetic oligonucleotide primer may be prepared by standard techniques (e,g, as described in Sambrook J, Fritsch E F, Maniatis T (1989) Molecular cloning: a laboratory manual ($2^{nd}$ edn.) Cold Spring Harbor Laboratory, Cold Spring Harbor, N.Y.) on the basis of the mature part of the amino acid sequence in SEQ ID NO: 2 or the corresponding part of the DNA sequence. It may be a degenerate probe and will typically contain at least 20 nucleotides.

Screening of Eukaryotic DNA Library

A polypeptide with lipoxygenase activity may be obtained by a method comprising:

a) preparing a eukaryotic DNA library, b) screening the library to select DNA molecules which hybridize to the probe described above, c) transforming host cells with the selected DNA molecules, d) cultivating the transformed host cells to express polypeptides encoded by the DNA molecules, and e) assaying the expressed polypeptides to select polypeptides having lipoxygenase activity.

The eukaryotic DNA library may be prepared by conventional methods. It may include genomic DNA or double-stranded cDNA derived from suitable sources such as those described above.

Molecular screening for DNA sequences may be carried out by polymerase chain reaction (PCR) followed by hybridization.

In accordance with well-known procedures, the PCR fragment generated in the molecular screening may be isolated and subcloned into a suitable vector. The PCR fragment may be used for screening DNA libraries by e.g. colony or plaque hybridization.

Hybridization

The hybridization is used to indicate that a given DNA sequence is analogous to a nucleotide probe corresponding to a DNA sequence of the invention. The hybridization may be done at low, medium or high stringency. One example of hybridization conditions is described in detail below.

Suitable conditions for determining hybridization between a nucleotide probe and a homologous DNA or RNA sequence involves presoaking of the filter containing the DNA fragments or RNA in 5×SSC (standard saline citrate) for 10 min, and prehybridization of the filter in a solution of 5×SSC (Sambrook et al. 1989), 5× Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6-13), $^{32}$P-dCTP-labeled (specific activity>1×10$^9$ cpm/µg) probe for 12 hours at approx. 45☐ C. The filter is then washed two times for 30 minutes in 2×SSC, 0.5% SDS at a temperature of at least 55☐ C, particularly at least 60☐ C, more particularly at least 65☐ C, e.g. at least 70☐ C, or at least 75☐ C Molecules to which the oligonucleotide probe hybridizes under these conditions are detected using an x-ray film.

Alignment and Identity

The nucleotide sequence of the invention may have an identity to the disclosed sequence of at least 75% or at least 85%, particularly at least 90% or at least 95%, e.g. at least 98%.

For purposes of the present invention, alignments of sequences and calculation of identity scores were done using a Needleman-Wunsch alignment (i.e. global alignment), useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment is from the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

Use of Lipoxygenase

A manganese lipoxygenase such as that described above may be used in the following application, e.g. in analogy with the indicated publications.

The lipoxygenase can be used as an additive to dough for baked products such as bread, biscuits and cakes. Thus, the lipoxygenase can be used in a process for making bread, comprising adding the lipoxygenase to a dough, kneading the dough and baking the dough to make the baked product. SU 426640 A, JP 58190346 A[SLK1], JP 1165332 A[SLK2], JP 8322456,[SLK3] JP 10028516[SLK4], JP 08322456, JP 2964215. It can also be used in the preparation of noodles as described in JP 11299440 A.

The lipoxygenase may be used for bleaching, e.g. bleaching of beta-carotene, wheat flour or wheat dough. U.S. Pat. Nos. 1,957,333-1,957,337.

It can also be used for oxidizing mixtures of fatty acids to hydroperoxy fatty acids, as accelerators of lipid peroxidition, and as analytic tools to estimate linoleic and linolenic acids contents of certain oils.

The invention provides a detergent composition comprising the lipoxygenase and a surfactant, particularly an anionic surfactant such as LAS (linear alkyl-benzene sulfonate). Advantageously, the lipoxygenase has good stability in the presence of such surfactants. The detergent may be formulated as described in U.S. Pat. No. 3,635,828 [SLK5]or U.S. Pat. No. 5,789,362[SLK6]. The lipoxygenase can also be used to bleach stains from fabrics or hard surfaces as described in DK 9800352[SLK7]. Advantageously, The lipoxygenase can be used for modification of starch as mentioned in JP 09163953, EP772980, JP 2000-106832. Also it can be used for protein modification as described in EP 947142, DE 19840069 or JP 61078361, or modification of oil (production of conjugated fatty acid) as mentioned in JP 5905128, U.S. Pat. No. 3,729,379.

The lipoxygenase can be used for cross-linking a protein by oxidases, such as laccase, bilirubin oxidase etc. EP 947142.

The lipoxygenase can be used to obtain improved glutinousness and improved flavor of marine paste product such as Kamaboko, Hanpen, by adding lipoxygenase to fish meat. JP 61078361.

The lipoxygenase can be used to produce a process tomato product. It can be used for tomato pasta, salsa, ketchup and so on. EP 983725.

The lipoxygenase can be used for production of hydroperoxy fatty acid by reacting lipoxygenase with unsaturated 4-24C fatty acid. JP 11029410.

The hydroperoxides of linoleic acid or linolenic acid can be converted further to e.g. growth regulatory hormone jasmonic acid, and the product from arachidonic acid can be converted to physiological effectors leukotrienes and lipoxins.

Application of lipoxygenase should not be limited to the examples mentioned above. Since hydroperoxide, the product of lipoxygenase reaction, is good oxidant to create radical, lipoxygenase can be used for any other applications utilizing oxidation reaction, such as bleaching of food material or textile dyes, or polymerization of chemical compounds to produce plastic material or fiber.

Assay for Lipoxygenase Activity

The lipoxygenase activity was determined spectrophotometrically at 25° C. by monitoring the formation of hydroperoxides. For the standard analysis, 10 µL enzyme was added to a 1 mL quartz cuvette containing 980 µL 25 mM phosphate buffer (pH 7.0) and 10 µL of substrate solution (10 mM linolenic acid dispersed with 0.2%(v/v) Tween20). The enzyme was typically diluted sufficiently to ensure a turnover of maximally 10% of the added substrate within the first minute. The absorbance at 234 nm was followed and the rate was estimated from the linear part of the curve. One unit causes an increase in absorbance at 234 nm of 0.001/min.

Determination of Substrate Specificity

The substrate specificity of the lipoxygenase was studied using the standard assays condition with a number of different compounds as substrate. All substrates were produced as dispersions with 0.2%(v/v) Tween20. The amount of compound added to make up these stock solutions was determined by mass, since viscosity made accurate measurement of volume impossible. The limiting rate constant and the specificity constant were determined by varying the amount of substrate added in the assays. The resulting rates were plotted against the concentration of substrate used. Finally, the plots were fitted by non-linear least squares regression to the theoretical hyperbolic curve of the Michaelis-Menten equation. The cis-trans-conjugated hydro(pero)xy fatty acids were assumed to have a molecular extinction coefficient of 23,000 $M^{-1}$ $cm^{-1}$.

EXAMPLES

Materials and Methods

Molecular cloning techniques are described in Sambrook et al. (1989).

The following commercial plasmids and E. coil strains were used for sub-cloning and DNA library construction:
pT7Blue (Novagen)
pUC19 (TOYOBO, Japan)
E. coli JM109 (TOYOBO, Japan)
E. coli DH12□ (GIBCO BRL, Life Technologies, USA)
The following commercial Kits were used for cDNA cloning;
cDNA Synthesis Kit (Takara, Japan)
Marathon cDNA Amplification Kit (Clontech, USA)
Oligo dT cellulose powder (Invitrogen, Netherlands)
Labeling and detection of hybridization probe was done using DIG-labeling and detection Kit (Boehringer Mannheim). Nylon membrane Hybond-N+ (Amersham, England) was used for DNA transfer for both southern blotting and colony hybridization.

Media and Buffer Solution

COVE-ar: per liter 342.3 g sucrose, 20 ml COVE salt solution, 10 mM acrylamide, 15 mM $CSCl_2$, 30 g Agar noble (Difco)

COVE2-ar: per liter 30 g sucrose, 20 ml COVE salt solution, 10 mM acrylamide, 30 g Agar noble (Difco)

COVE salt solution: per liter 26 g KCl, 26 g $MgSO_4$-$7H_2O$, 76 g $KH_2PO_4$, 50 ml Cove trace metals.

Cove trace metals: per liter 0.04 g $NaB_4O_7$-$10H_2O$, 0.4 g $CuSO_4$-$5H_2O$, 1.2 g $FeSO_4$-$7H_2O$, 0.7 g $MnSO_4$-$H_2O$, 0.7 g $Na_2MoO_2$-$2H_2O$, 0.7 g $ZnSO_4$-$7H_2O$.

AMG trace metals: per liter 14.3 g $ZnSO_4$-$7H_2O$, 2.5 g $CuSO_4$-$5H_2O$, 0.5 g $NiCl_2$, 13.8 g $FeSO_4$, 8.5 g $MnSO_4$, 3.0 g citric acid.

YPG: per liter 4 g yeast extract, 1 g $KH_2PO_4$, 0.5 g $MgSO_4$-$7H_2O$, 15 g glucose, pH 6.0.

STC: 0.8 M Sorbitol, 25 mM Tris pH 8, 25 mM $CaCl_2$.

STPC: 40% PEG4000 in STC buffer.

Cove top agarose: per liter 342.3 g sucrose, 20 ml COVE salt solution, 10 mM Acelamide, 10 g low melt agarose.

MS-9: per liter 30 g soybean powder, 20 g glycerol, pH 6.0.

MDU-2 Bp: per liter 45 g maltose-1$H_2O$, 7 g yeast extract, 12 g $KH_2PO_4$, 1 g $MgSO_4$-$7H_2O$, 2 g $K_2SO_4$, 5 g Urea, 1 g NaCl, 0.5 ml AMG trace metal solution pH 5.0.

Materials alpha-$^{32}$P-dCTP (3000 Ci/mmol), dNTPs, alpha-$^{33}$P-ddNTPs, Hybond-N membranes, and DNA labeling beads (-dCTP), T-primed first-strand kit, and Thermo Sequenase kits were from Amersham Pharmacia Biotech (Uppsala, Sweden). TA cloning kits were from Invitrogen (Groningen, The Netherlands). Taq DNA polymerase and the enhanced avian RT-PCR kit were from Sigma (St. Louis, Mo.). Restriction enzymes were from New England BioLabs (Beverly, Mass.).

G. graminis was obtained and grown as described by Su and Oliw (supra). Qiagen plant RNeasy mini and OIAquick gel extraction kits were from Merck Eurolab (Stockholm, Sweden). Degenerate primers for PCR were obtained from TIB Molbiol (Berlin, Germany), whereas sequencing primers were purchased from CyberGene (Huddinge, Sweden). 5'-RACE and reverse transcription of total RNA was performed with a kit (5'RACE system for rapid amplification of cDNA ends) from Life Technologies (Täby, Sweden).

Example 1

Determination of Partial Peptide Sequences of LOX from G. graminis

A fungal strain of Gaeumannomyces graminis var. tritici was cultivated and lipoxygenase was recovered essentially as described in Chao Su and Ernst H. Oliw, J. Biological Chemistry, 273 (21), 13072-13079 (1998).

To obtain data from the N-terminal part of the enzyme, approximately 10 mg of enzyme was analyzed directly by using traditional edman degradation on the 494 Protein Sequencer, Applied Biosystems according to the manufacturer's instructions.

Another 40 microgram of sample was lyophilized down to around 20 μl and added 20 μl SDS-sample buffer containing DTT before incubation 30 min at 37° C. and then boiling the sample for 3 min. 5 μl 0.5 M iodoacetamide in 1 M Tris-HCl, pH 7.5 was then added and the sample was incubated 20 min at room temperature prior to running the sample on SDS-PAGE (4-20%, Novex) according to the manufacturer's instructions. The gel was stained according to standard procedures from Novex.

The gelpiece (60 kDa) was subsequently cut out and minced with a blade. The gel pieces were washed 2× in 0.5 M tris pH 9.2/ACN (1:1) for 45 min at 37° C. The gel pieces were treated with 100% ACN for 10 min to introduce shrinking of the pieces. The ACN was removed and the pieces dries in speed-Vac. 200 ml 0.1 M NH4CO3 (AMBIC) was added and incubated for 15 min. AMBIC was removed and 100 ml ACN added. Again incubation for 10 min followed by removal of ACN and drying in speed-vac. The cycle with AMBIC was repeated 2×. After the last drying step 20 ml 0.05 mg/ml trypsin in 0.1 M tris pH 9.2, 10% ACN was added. Incubation for 10 min. Then 300 ml 0.1 M tris pH 9.2, 10% ACN was added. Incubation was continued O.N. at 37° C. The supernatant was then removed (saved for control) and the peptides extracted from the gel by adding 30 ml 10% TFA. After 5 min the TFA was withdrawn and collected. Further extraction was done 2× by adding 150 ml 0.1% TFA, 60% ACN to the gel pieces and incubate for 30 min at 37° C. All extracts were collected (30 ml+150 ml+150 ml) and concentrated in the speed-vac to 50 ml. A sample of the concentrate (5 ml) was run on RP-HPLC on a Vydac C-18 column using solvent system of TFA/isopropanol to see if any peptides were present. The rest of the sample was run to collect the peptides. Controls with blank gel pieces were run in parallel. To minimize loss of peptide, selected fractions were sequenced directly without any repurification.

The resulting N-terminal sequence is shown as SEQ ID NO: 21, and two internal peptides (denoted fr 29 and 34) are shown as SEQ ID NOS: 19 and 20.

Further, around 100 μg lipoxygenase was added 40 μl 0.05 M potassium phosphate, 10 mM EDTA, 1% Triton X-100, 0.05% SDS, pH 7.3 and heated to 90° C. for 4 min and allowed to cool. Then the sample was added 25 mU O-glycosidase (BSA free) and 800 mU EndoF glycosidase (Boehringer) and left over night at 37° C. The sample was then added 75 gl SDS sample buffer and run on SDS-PAGE (Novex 4-20%) in 7 lanes according to the manufacturer's instructions.

The 60 kDa bands were cut out from the gel minced and washed twice in eppendorf tubes with 400 μl of 0.5 M Tris-HCl, pH 9.2:ACN 1:1 for 45 min at 37° C. The gel pieces were then treated with 200 μl ACN for 10 min and then dried in the speed vac. 400 μl NH4HCO3 was added and left for 10 min before removing the supernatant and treating the pieces with another 200 μl of ACN for 10 min and then drying. 400 μl H2O was added and the sample left for 10 min before repeating the procedure with ACN again. The gel pieces was then added 25 μl 0.1 mg/ml trypsin+300 μl 0.1 M Tris-HCl, 10% ACN, pH 9.2 and left over night at 37° C. After incubation 35 μl of 10 TFA was added and the supernatant were taken after 30 min for HPLC (Vydac C18, gradient to 80% acetonitril in 0.1% TFA). The gel pieces were then further extracted twice with 150 μl 0.1% TFA, 60% acetonitril. The supernatant was taken and evaporated in the speed vac to around 50 μl before adding further 100 μl 0.1% TFA and then re-evaporating down to 50 μl which was then run on the HPLC.

Three amino acid sequences (denoted fr 20, 21 and 25) were obtained, as shown in SEQ ID NOS: 16,17 and 18.

Example 2

Cloning of Genomic and cDNA Clone of LOX From *G. graminis*

Preparation of Fungal Chromosomal DNA

A fungal strain *Gaeumannomyces graminis* var. *triftici* was cultivated in the YPG (composed per liter: 4 g Yeast extract, 1 g $KH_2PO_4$, 0.5 g $MgSO_4$ $7H_2O$, 15 g Glucose, pH 6.0) with gentle agitation at 25° C. for 6 days. Mycelia was collected by filtration using Mira-cloth (Calbiochem, USA) and washed with deionized water twice. After briefly dried on paper filter, mycelia was frozen by liquid nitrogen and ground by motor on dry ice. Around 0.2 g ground mycelia was put into a 1.5 ml eppendorf tube and suspended in 0.5 ml of buffer solution composed with 100 mM NaCl, 25 mM EDTA, 1% SDS and 50 mM Tris-HCl (pH 8). After addition of 3 micro-l of 25 mg/ml proteinase K, the tube was incubated at 65° C. for 30-60 minutes. The solution was extracted with the same volume of phenol and DNA was precipitated with 0.7 volume of isopropanol at −20° C. The pellet was re-suspended in 0.5 ml of sterilized water and remaining RNA was digested by 50 micro-g of RNase at 37° C. for 30 minutes. DNA was phenol extracted and ethanol precipitated again. The pellet was resuspended in appropriate amount of sterilized water.

Preparation of mRNA and Synthesis of cDNA

A fungal strain *Gaeumannomyces graminis* var. *tritici* was cultivated in the YPG with gentle agitation at 25° C. for 6 days. After the lipoxygenase activity was confirmed, mycelia was collected and ground on dry ice as mentioned before to be used for the preparation of total RNA with phenol-chloroform method. Purification of mRNA from total RNA was performed with Oligo dT cellulose powder (Invitrogen, Netherland).

Synthesizing of cDNA was done with cDNA Synthesis Kit (Takara, Japan). The first strand cDNA was synthesized using 5-6 micro-g of heat denatured mRNA as the template in the mixture containing 1.0 mM each of dNTP, 4 μg of oligo$(dT)_{1B}$ and 2 μg of random primer and 100 U of reverse transcriptase and $1^{st}$ strand synthesis buffer. In total 50 μl of reaction mixture was kept at room temperature for 10 min, then incubated at 42° C. for 1 hour. After the incubation, the reaction mixture was chilled on ice for 2 min and subjected to $2^{nd}$ strand cDNA synthesis. 1138 U of *E. coli* DNA polymerase and 5 µl of *E. coli* RNase H/*E. coli* DNA ligase mixture and $2^{nd}$ DNA synthesis buffer was added to the $1^{st}$ strand synthesis mixture and diluted up to 240 µl with DEPC-$H_2O$. The reaction mixture was incubated at 12° C. 1 hour, 22° C. 1 hour and 70° C. 10 min. Then 10 U of T4 DNA polymerase was added to the reaction mixture and incubated at 37° C. 10 min. Synthesized cDNA was subjected to agarose gel electrophoresis to confirm the quality.

Isolation of a Partial Clone of LOX Gene by PCR

The following primers were designed and synthesized based on the amino acid sequences determined in Example 1. The nucleotide sequence of linoleate diol synthase of *Gaeumannomyces graminis* (Genbank Accession #: AF124979) was used as a reference of codon usage.

Primer 1 for N-term side: SEQ ID NO: 9 (corresponding to amino acids 1-5 of N-terminal SEQ ID NO: 21).

Primer 2 for C-term side 1: SEQ ID NO: 10 (corresponding to amino acids 18-25 of fr 34, SEQ ID NO: 20).

Primer 3 for C-term side 2: SEQ ID NO: 11 (corresponding to amino acids 6-15 of fr 34, SEQ ID NO: 20).

Polymerase chain reaction (PCR) was employed using 0.6 µg of chromosomal DNA of *G. graminis* as the template in 50 micro-I reaction mixture containing 2.5 mM each of dNTP, 20 pmol each of primer 1 and 2, 2.5 units of LA taq polymerase (Takara, Japan) and GC buffer I supplied by Takara for LA taq. Reaction condition was shown below. LA taq polymerase was added to the reaction mixture after step 1.

| Step | Temperature | Time |
| --- | --- | --- |
| 1 | 98° C. | 10 mins |
| 2 | 96° C. | 20 sec |
| 3 | 53° C. | 45 sec |
| 4 | 72° C. | (27 + 3 × cycle) sec |
| 5 | 72° C. | 10 mins |

*Step 2 to Step 4 were repeated 50 times.

Second PCR reaction was employed in the reaction mixture described above but using 2 µl of first PCR product as template and primer 3 instead of primer 2. Reaction condition was the same as described above except step 2 to step 4 were repeated 30 times.

Amplified 1 kb fragment was gel-purified using QIAquick™ Gel Extraction Kit (Qiagen) and subcloned into pT7Blue. Sequence of the PCR clone was determined as shown in SEQ ID NO: 3. From the deduced amino acid sequence of the PCR fragment, the primer 1 turned out to be hybridized to elsewhere than expected, however, amino acid sequence 250599Bfr25 (SEQ ID NO: 18) determined in Example 1 was found in continuous 216 amino acids sequence in the PCR fragment (SEQ ID NO: 8). Identity search showed that the 216 amino acid sequence had the highest identity to Human 15S Lipoxygenase (Genbank U78294, GENESEOP W93832), Human arachidonate 12-Lipoxygenase (Swiss-Prot P18054) and *Plexaura homomalla* 8R-Lipoxygenase (GenBank AF003692, SPTREMBL O16025). The results indicated that the obtained PCR fragment contained lipoxygenase gene. The highest score of identity was obtained with Human 15S and was less than 25%.

Cloning of Genomic LOX Gene

To obtain a full-length genomic clone, southern blotting was employed on genomic DNA of *G. graminis* using PCR fragment as a probe. Based on the result, genomic DNA was digested with SalI and separated on 1.0% agarose gel. Around 6 kb of DNA digestion was recovered from the gel and ligated with BAP treated pUC19 lineared by SalI. Ligation mixture was transformed into *E. coli* DH12S to construct a partial genomic library. It was screened by colony hybridization using the PCR fragment as probe, and a positive *E. coli* colony was isolated and the plasmid, termed pSG16, was recovered. The plasmid pSG16 contained a 6 kb SalI fragment from *G. graminis*. Out of 6 kb of this fragment, sequence of 4.1 kb length including the PCR clone was determined as shown in SEQ ID NO: 4. The largest open reading frame (ORF) contained the above-mentioned 216 amino acid sequence as well as the similar sequences to fr 20, 21, 29 and 34, SEQ ID NOS: 16, 17, 19 and 20 but not the N-terminal sequence (SEQ ID NO: 21) determined in example 1. Two other small ORFs were found in the upstream of the largest ORF, but none of them had the N-terminal sequence neither. To find the right initial ATG codon, cDNA cloning was necessary.

Isolation of cDNA Clone of LOX Gene

Total RNA was extracted from the mycelia producing lipoxygenase and subjected for mRNA preparation by Oligo dT cellulose powder. The cDNA was synthesized from the mRNA using cDNA Synthesis Kit (Takara, Japan) and aiming to obtain full-length cDNA, 1-4 kb of cDNA was gel-purified to be subjected for the construction of a partial cDNA library. Library was constructed by ligating with the adaptor of Marathon cDNA Amplification Kit (Clontech, USA), which allows the amplification of aimed cDNA with the Adaptor Primer (AP1) and a custom primer designed for the internal sequence of aimed clone.

For the amplification of cDNA of LOX, two primers, primer 4 (SEQ ID NO: 12) and primer 5 (SEQ ID NO: 13), were designed based on the sequence of genomic clone. C-terminal part was amplified with primer 4 and AP1, and N-terminal part was amplified with primer 5 and AP1.

PCR reaction mixture comprised of 2.5 mM dNTP, 30 pmol each of primer 4 and AP1 or primer 5 and AP1, 5 units of LA taq polymerase (Takara) and supplied GC buffer 1. Reaction condition was shown below. LA taq polymerase was added to the reaction mixture after step 1.

| Step | Temperature | Time |
| --- | --- | --- |
| 1 | 98° C. | 5 mins |
| 2 | 95° C. | 30 sec |
| 3 | 74° C. | 15 sec |
| 4 | 68° C. | 3 mins |
| 5 | 95° C. | 30 sec |
| 6 | 95° C. | 5 mins |
| 7 | 54° C. | 30 sec |
| 8 | 68° C. | 15 sec |

*Step 2 to Step 4 were repeated 15 times and the temperature of Step 3 was decreased 4° C. after each 3 repeat. Step 6 to Step 8 were repeated 20 times.

As the results, 0.6 kb and 1.6 kb fragments were amplified for 5'-end and 3'-end respectively and the sequences were determined as shown in SEQ ID NO: 5 and SEQ ID NO: 6. Based on the sequence around the predicted initial ATG and stop codon TAA, the primer 6 (SEQ ID NO: 14) and primer 7 (SEQ ID NO: 15) were designed for the amplification of end-to-end cDNA. Also desired restriction enzyme sites were introduced at both ends for further plasmid construction.

Reaction mixture contained 0.08 µg of cDNA library, 2.5 mM dNTP, 30 pmol each of primer 6 and 7, 1 units of LA taq polymerase (Takara) and GC buffer. Reaction condition was shown below. LA taq polymerase was added to the reaction mixture after step 1.

| Step | Temperature | Time |
|------|-------------|------|
| 1 | 98° C. | 10 mins |
| 2 | 96° C. | 20 sec |
| 3 | 53° C. | 45 sec |
| 4 | 72° C. | (27 + 3 × cycle) sec |
| 5 | 72° C. | 10 mins |

*Step 2 to Step 4 were repeated 50 times.

PCR amplified 1.9 kb fragment was isolated and cloned into pT7Blue resulting in pSG26. Sequence of the full-length cDNA was determined. The deduced open reading frame consisted of of 1857 bp, which corresponded to 618 amino acids and a molecular mass of 67600 Da. Comparison with the genomic sequence turned out that the LOX gene contained one intron in the N-terminal side. Predicted N-terminal sequence by signal sequence determination program is "ALP-LAAEDAAAT". Identity search with the full-length amino acid sequence showed that it had the highest identity to Human 15S Lipoxygenase (Genbank Accession number w93832), less than 25%.

The plasmid pSG26 was transformed in *E. coli* JM109 and deposited at DSMZ as DSM 13586 with the accession date 5 Jul. 2000.

Example 3

Expression of *G. graminis* LOX in *A. oryzae*

Host organism

*Aspergillus oryzae* BECh2 is described in Danish patent application PA 1999 01726. It is a mutant of JaL228 (described in WO98/123000), which is a mutant of IFO4177.

Transformation of *A. oryzae*

*Aspergillus oryzae* strain BECh2 was inoculated in 100 ml of YPG medium and incubated at 32° C. for 16 hours with stirring at 80 rpm. Grown mycelia was collected by filtration followed by washing with 0.6 M KCl and re-suspended in 30 ml of 0.6 M KCl containing Glucanex® (Novo Nordisk) at the concentration of 30 µl/ml. The mixture was incubated at 32° C. with the agitation at 60 rpm until protoplasts were formed. After filtration to remove the remained mycelia, protoplasts were collected by centrifugation and washed with STC buffer twice. The protoplasts were counted with a hematitometer and re-suspended in a solution of STC:STPC: DMSO (8:2:0.1) to a final concentration of $1.2 \times 10^7$ protoplasts/ml. About 4 µg of DNA was added to 100 µl of protoplast solution, mixed gently and incubated on ice for 30 minutes. 1 µl STPC buffer was added to the mixture and incubated at 37° C. for another 30 minutes. After the addition of 10 ml of Cove top agarose pre-warmed at 50° C., the reaction mixture was poured onto COVE-ar agar plates. The plates were incubated at 32° C. for 5 days.

SDS-PAGE

SDS polyacrylamide electrophoresis was carried out using the commercialized gel PAGEL AE6000 NPU-7.5L (7.5T%) with the apparatus AE-6400 (Atto, Japan) following the provided protocol. 15 µl of sample was suspended in 15 µl of 2×conc. of sample loading buffer (100 mM Tris-HCl (pH 6.8), 200 mM Dithiothreitol, 4% SDS, 0.2% Bromophenol blue and 20% glycerol) and boiled for 5 minutes. 20 µl of sample solution was applied to a polyacrylamide gel, and subjected for electrophoresis in the running buffer (25 mM Tris, 0.1% SDS, 192 mM Glycine) at 20 mA per gel. Resulting gel was stained with Coomassie brilliant blue.

Construction of Expression Plasmid

The plasmid pSG26 containing cDNA of *G. graminis* LOX was digested by Bg/ll and Xhol and 1.9 kb of fragment which contained the LOX gene was ligated with pMT2188 digested with BamHl and Xhol. The plasmid pMT2188 has a modified *Aspergillus niger* neutral amylase promoter, *Aspergillus nidulans* TPI leader sequence, *Aspergillus niger* glucoamylase terminator, *Aspergillus nidulans* amdS gene as a marker for fungal transformation and *S.cerevisiae* ura3 as the marker for *E.coli* transformation. Transformation was done with *E. coli* DB6507 in which pyrF gene is deficient and can be complemented with *S.cerevisiae* Ura3. Resulting plasmid was termed pSG27.

Expression of *G. graminis* LOX in *A. oryzae*

*A. oryzae* BECh2 was transformed with the plasmid pSG27 and selection positive transformants were isolated. Transformants were grown on COVE 2-ar at 32° C. for 5 days and inoculated to 100 ml of MS-9 shaking flask. After the cultivation with vigorous agitation at 32° C. for 1 day, 3 ml of each culture was transferred to 100 ml of MDU-2 Bp in shaking flask to cultivate at 32° C. for 3 days. Culture broth was centrifuged at 3500 rpm for 10 minutes and supernatant was collected. Lipoxygenase activities of the supernatant were determined spectrophotometrically as described before. Positive transformants showed about 50,000U/ml culture broth while untransformed *A. oryzae* BECh2 showed no activity. Culture supernatant was also subjected to SDS-PAGE analysis. Positive transformants showed 90-110 kDa smear band which indicated the protein was heavily glycosylated. Untransformed *A.oryzae* BECh2 did not show any major band.

Example 4

Purification of Recombinant Lipoxygenase

One gram of crude lyophilised lipoxygenase prepared as in the previous example was dissolved in 40 mL 25 mM Tris-HCl (pH 8.0) and then filtered (0.45 µm, type Millex-HV, Millipore). The above and subsequent steps were all carried out at room temperature. The filtrate was loaded on a SP-Sepharose Fast Flow (2.6×14 cm) with 25 mM Tris-HCl (pH 8.0) at 1 mL/min. The column was then washed with the same buffer at 2.5 mL/min until baseline was reached (approximately 4 column volumes). The bound protein was then eluted with a linear gradient from 0 to 330 mM NaCl in 25 mM Tris-HCl (pH 8.0) in 2 column volumes. Fractions of 10 mL were collected. The column was cleaned with 1 M NaCl in 25 mM Tris-HCl (pH 8.0). The fractions containing the majority of pure lipoxygenase, as estimated by SDS-PAGE and by activity assay, were pooled and concentrated using an Amicon cell (10,000 NMWL, YM10, Millipore). The enzyme was finally transferred into 50 mM sodium phosphate (pH 7.0) by dialysis and stored in aliquots at –20° C. until use.

SDS-PAGE analysis showed that the lipoxygenase had been purified to homogeneity. The enzyme was found to have an estimated molecular weight of 90-110 kDa, somewhat higher than the theoretical value based on the amino acid sequence (65.6 kDa). This was taken as an indication of glycosylation. The protein was found to have a very high isoelectric point as demonstrated by the successful purification employing cation exchange chromatography.

Example 5

Determination of the Gene and the Deduced Protein Sequence of Mn-lipoxygenase

1. Amino Acid Sequences of Internal Peptides and the C-Terminal Amino Acids of Manganese Lipoxygenase Manganese lipoxygenase was purified to homogeneity as described by Su and Oliw (supra), using a strain of *G. graminis* (different from the previous examples). Internal peptides were generated, purified and sequenced by the Sanger method essentially as described for another protein of *G. graminis* (Hornsten L, Su C, Osbourn A E, Garosi P, Hellman U, Wernstedt C and Oliw E H, Cloning of linoleate diol synthase reveals homology with prostaglandin H synthases. J Biol Chem 274(40): 28219-24, 1999). The N-terminal amino acid of Mn-lipoxygenase was blocked, but four C-terminal amino acid was obtained by C-terminal sequencing.

(i) C Terminal Amino Acid Sequence

These C-terminal amino acids were FLSV.

(ii) Internal Amino Acid Sequences

The following eight internal amino acid sequences were obtained (where (K), (K/R) and (E) denotes the fact that Lys-C, trypsin and V8 cleaves peptides at the C-terminal side of K residues, K or R residues, and E residues, respectively):

(K)LYTPQPGRYAAACQGLFYLDARSNQFLPLAIK (amino acids 205-237 of SEQ ID NO: 23 with the substitution K206L)

(K/R)HPVMGVLNR (amino acids 295-304 of SEQ ID NO: 23 with Lys or Arg at position 295)

(K/R)LFLVDHSYQK (amino acids 196-205 of SEQ ID NO: 23 with Lys or Arg at position 196)

(E)M?AGRGFDGKGLSQG(W/M)PFV (amino acids 569-587 of SEQ ID NO: 23, except that amino acid 570 is uncertain Met and amino acid 584 is Trp or Met)

(K/R)GLVGEDSGPR (amino acids 365-375 of SEQ ID NO: 23 except that amino acid 365 was found to be Lys or Arg and 368 Val)

(K)TNVGADLTYTPLD/AD/WK/LP/ND/NE (amino acids 237-255 of SEQ ID NO: 23 except that amino acid 242 was found to be Ala, 250 Asp or Ala, 251 and Asp or Trp)

(K)G/F SGVLPLHPAw (amino acids 472-483 of SEQ ID NO: 23, except that amino acid 473 was found to be Gly or Phe, and amino acid 483 uncertain Trp)

(K) QTVDDAFAAPDLLAGNGPGRA (amino acids 532-553 of SEQ ID NO: 23 except that amino acid 536 was found to be Asp, and 552 Arg)

2. RT-PCR with Degenerate Primers Generated cDNA of Mn-lipoxygenase

This part of the invention was difficult due to the high GC content of the genome of *G. graminis*.

Methods for isolation of total RNA from *G. graminis* and transcription of mRNA to cDNA had to be optimised. cDNA was often contaminated with genomic DNA in spite of digestion with DNAses and other precautions.

After considerable experimentation, using over 30 degenerate primers in various combinations, the first cDNA clone of Mn-lipoxygenase could be obtained by RT-PCR. It was obtained by the following degenerate primers, which were based on internal peptides 1 and 2 and above.

(SEQ ID NO: 25)
Mn60 (5'-AACCAGTTCCTSCCSCTCGCSATCAA), (SEQ ID NO: 26)
Mn15R (5'-GTCGAGGTAGAAGAGGCCCTGRCAVGC), (SEQ ID NO: 27)
EO3a (5'-CATCCSGTSATGGGYGTSCTBAA), (SEQ ID NO: 28)
EOr3a (5'-CGGTTSAGGACRCCCATVACVGGRTG).

The primers Mn60 and EOr3A generated an RT-PCR band of about 230-bp and the primers EO3A and Mn15R generated an RT-PCR band of about 220-bp. A sense primer from this sequence (MnS2: 5'-CCGTTCAGCGTCGAGAGCAAGG (SEQ ID NO: 29)) and an antisense primer from the other sequence (MnS1, 5'-TCTCGGGGATCGTGTGGAA-GAGCA (SEQ ID NO: 30)) amplified a fragment of 337-bp. The amplicon was sequenced and it contained the amino acid sequence of peptide1 in one of the reading frames. The amplicon was used as probe for Northern blot analysis and for screening of a genomic library (Hornsten et al., supra).

3. Screening of a Genomic Library of *G. graminis*

A genomic library of *G. graminis* in Lambda ZAP II was obtained as described by Bowyer P et al., Science 267(5196): 371-4, 1995. It was screened with a probe of 0.33-kb from the cDNA sequence. Screening of over 100 000 plagues yielded 11 positive clones, which were plague purified by 2-3 additional rounds of phage screening. The Bluescript SK phagemid was excised with helper phage following published methods. Restriction enzyme analysis showed that all rescued phagemids contained the same insert of 8-kb.

4. Sequencing of the Gene and Coding Region of Mn-LO of *G. graminis*

Sequencing was performed of both strands using two different methods based on cycle sequencing. The sequencing was difficult due to the high GC content of the gene (over 60% GC).

3.4-kb of the genome of *G. graminis* was sequenced and the sequence of 2725 nucleotides of the Mn-lipoxygenase gene included an intron of 133-bp. The gene of Mn-lipoxygenase was identified by 5'-RACE from the starting point of transcription of 2 mRNA, a$^1$gcaggttc, and the protein translation start point A$^{72}$TG (at nucleotide position 72). The C-terminal amino acids FLSV were found with the stop codon at position 2060-2062. Over 0.6-kb of the 3'-untranslated region was sequenced and tentative polyadenylation signals were found as shown below:

5-RACE and cDNA sequencing was used to confirm the deduced open reading frame and the exon-intron borders. The transcription start point, the translation start point and the translation end were determined as shown in SEQ ID NO: 22 and 23.

The Intron was found to have a length of 133 bp and to have the sequence shown as SEQ ID NO: 24. It was found to be located between nucleotides 372 and 373, i.e. between Ser108 and Arg109 of SEQ ID NO: 22.

Example 6

Expression of Native and Genetically Modified Mn-lipoxygenase

We have subcloned a genomic segment (3-kb) containing the coding region of the Mn-lipoxygenase gene from the Bluescript SK phagemid into the multi cloning site (with SpeI and NsiI sites) of the plasmid pGEM-5Zf (Promega) using the restriction enzymes SpeI and NsiI.

The 5'-end and the intron were modified as follows. pGEM-5Z with the insert was cleaved with SpeI and BseRI, which cut out the 5'-end of the gene and part of the genomic sequence with the intron (1323-bp). This piece was replaced in pGEM with a cDNA sequence of about 405-pb, which was obtained by cleavage of a PCR product of 448-bp with SpeI and BseR1. This vector is designated pGEM_Met. The PCR product was generated with a sense primer specific to the translation start region (and with SpeI and NdeI site in the 5'-end of the primer, 5'-TTACTAGTCATATGCGCTCCAG-GATCCTTGCT (SEQ ID NO: 31)), and a gene specific antisense primer located at the 3'-end of the BseR1 site. This cDNA part so inserted thus contained the beginning of the ORF (without the Intron positioned between nucleotides 372 and 373, between Ser108 and Arg109, as shown in the table above), so that the entire ORF was obtained in the vector pGEM_Met.

The 3'-end was modified with PCR, taking advantage of an BbvCI site about 130-bp from the stop signal. The sense primer was gene-specific and located at the 5'-side of the restriction site, whereas the antisense primer was designed from the nucleotides of the terminal amino acids and contained, in addition, NdeI and NsiI restriction sites. The pGEM_Met vector was cleaved with NsiI and BbvC1, and the excised fragment was replaced with the PCR product cleaved in the same way. This yielded the vector pGEM-Met_ter. The modified coding region of Mn-lipoxygenase in this vector can thus be excised with NdeI. All modifications have been confirmed by sequencing of the expression constructs.

1. Expression of Mn-Lipoxygenase in Procaryotic Cells (*E. coli*)

The expression vector pET-19b has been linearized with NdeI, and the modified coding region of Mn-lipoxygenase has been excised with NdeI and ligated into this vector for expression in *E coli*, as suggested by the manufacturer of the pET expression vectors (Stratagene). Studies of recombinant Mn-lipoxygenase expressed in *E. coli* is now in progress.

2. Expression of Mn-Lipoxygenase in Eukaryotic Cells (*Pichia pastoris, Saccharomyces cerevisiae, Aspergillus nidulans, Gaeumannomyces graminis*)

We plan to use the Pichia Expression kit with the pCIC9 or related vectors (Invitrogen), which has to be slightly modified to fit our modified coding region of Mn-lipoxygenase. It is possible that glycosylation of recombinant Mn-lipoxygenase may differ between different hosts. We therefore plan to investigate a series of eukaryotic expression systems in *Saccharomyces cerevisiae, Aspergillus nidulans, Gaeumannomyces graminis*. Glucosylation may improve the stability of the recombinant enzyme.

3. Expression of Mn-Lipoxygenase in Eukaryotic Cells (Insect Cells)

We plan to use the Drosophila Expression System (Schneider 2 cells) from Invitrogen using an expression vector without His tags at the C-terminal end.

4. Genetically modified Mn-Lipoxygenase for expression.

Our discovery that Mn-lipoxygenase belongs to the lipoxygenase gene family opens large possibilities for rational modification of the structure. The 3D sequence of several lipoxygenases are known and Mn-lipoxygenase shows significant amino acid identity along many α-helices of soybean lipoxygenase-1 (Prigge S T, Boyington J C, Gaffney B J and Amzel L M, Structure conservation in lipoxygenases: structural analysis of soybean lipoxygenase-1 and modeling of human lipoxygenases. *Proteins* 24(3): 275-91, 1996), which has been used for modeling of many lipoxygenases. Both the metal ligands and other structurally important amino acids of Mn-lipoxygenase will be mutated in order to increase the bleaching properties and oxidative properties of the enzyme.

4.1 Site directed mutagenesis of amino acids of important alpha-helices.

Amino acid sequences of Mn-lipoxygenase align with α-helix 9 (Prigge et al., supra), which contains the WLLAK sequence and two His residues, which likely are Mn ligands. Systematic changes of amino acids in this helix might have profound effect on enzyme activity and bleaching properties. In the same way, an amino acid sequence of Mn-Lipoxygenase align with α-helix 18, which contain iron ligands and likely Mn-ligands (His and Asn). Other predicted α-helices of Mn-lipoxygenase, which should be mutated, correspond to α-helices 7, 8, 10-17, 19-22 of soybean lipoxygenase-1 (Prigge et al., supra). We predict that some of these genetically modified Mn-lipoxygenases may have totally different properties, and the bleaching effect may be enhanced. Predicted Mn ligands thus are 3 His residues, one Asp residue and one Val residue. Mn-lipoxygenase likely belongs to enzymes of the "2-His-1-carboxyl facial triad".

4.2 Site directed mutagenesis of amino acids of the C-terminal end.

We plan to mutate the terminal Val to an Ile or to other residues and to determine the bleaching properties of the mutated form.

4.3 Mosaic Forms of Mn-lipoxygenase

In order to improve the properties of Mn-lipoxygenase we plan substitute various parts with the corresponding sequence of soybean lipoxygenase using the α-helix information described above.

Example 7

Screening of Eukaryotic DNA

To screen for homologous lipoxygenase genes in eukaryotic fungal strains, southern hybridization was performed on the genomic DNA from several fungal strains using cDNA of *Gaeumannomyces graminis* LOX gene as the probe. Strains of the following species were tested; *Pyricularia oryzae, Psaliota campestris, Penicillium roqueforti* and *Geotrichum candidum* ATCC34614. Genomic DNA was isolated as described in Example 2.

The probe was labeled with digoxigenin-dUTP using DIG DNA labeling Mix (Boehringer Mannheim) as follows; DIG labeled probe was prepared by PCR using primer 6 (SEQ ID NO: 14) and primer 7 (SEQ ID NO: 15) as the full-length cDNA of *G. graminis* LOX. PCR reaction mixture contained 0.1 µg of pSG26 as the template, 1.25 mM dNTP, 8% DIG DNA Labeling Mix, 30 pmol each of primer 6 and 7, 1 unit of LA taq polymerase (Takara) and GC buffer. Reaction conditions were as shown below. LA taq polymerase was added to the reaction mixture after step 1.

| Step | Temperature | Time |
|---|---|---|
| 1 | 98° C. | 10 mins |
| 2 | 94° C. | 2 mins |
| 3 | 60° C. | 30 sec |
| 4 | 72° C. | 2 mins |
| 5 | 72° C. | 10 mins |

*Step 2 to Step 4 were repeated 30 times.

PCR products were gel-purified and denatured by heating at 98° C. before use.

About 5 micro-g of DNA digested with restriction enzyme was separated on 1.0% agarose gel and denatured by soaking the gel in 0.2N HCl for 30 minutes and in 0.5N NaOH +1.5M NaCl for 30 minutes, then and neutralized in 1M Tris (pH 7.5)+1.5M NaCl for 30 minutes. Denatured DNA was then transferred to the nylon membrane by vacuum transfer with 20×SSC for 15 minutes. After fixing by UV irradiation, nylon membrane was used for the hybridization. Hybridization solution was composed with 5×SSC, 0.5% blocking reagent (Boehringer Mannheim), 0.1% N-lauroylsarcosine and 0.02% SDS. The nylon membrane was prehybridized with the hybridization solution at 60° C. for 1 hour. After that, the heat-denatured DIG-labeled probe was added to the hybridization solution and incubated at 60° C. overnight. Resulting membrane was washed with washing buffer comprising 2×SSC+0.1% SDS for 5 minutes at room temperature twice followed by washing with washing buffer 2 composed with 0.1×SSC+0.1% SDS for 15 minutes at hybridization temperature twice. Washed membrane was air-dried and used for the detection of DIG-labeled DNA by following the provided protocol of DNA detection Kit (Boehringer Mannheim).

As the result, *Pyricularia oryzae* showed clear positive signals and *Geotrichum candidum* showed very weak signals. The results indicate that *Pyricularia oryzae* has a lipoxygenase gene that has a high identity to *Gaeumannomyces graminis* LOX and *Geotrichum candidum* has a gene that has low identity to *G. graminis* LOX.

Example 8

Effect of pH on Mn-Lipoxygenase

The activity of lipoxygenase produced as in Example 4 was tested at various pH values. The enzyme was found to have a broad pH optimum with high activity in the range of pH 6-10 or 7-11 with linoleic acid or linolenic acid as substrate.

The stability of the enzyme was determined after 1 hour incubation at 40° C. at various pH values. The enzyme was found to have good stability in the pH range 4-10.

Example 9

Substrate Specificity of Lipoxygenase

The activity of lipoxygenase produced as in Example 4 was tested on various substrates as described above. The results are expressed as $k_{cat}$ (or $V_{max}$), $K_M$ and $k_{cat}/K_M$ according to the Michaelis-Menten equation:

| Substrate | $k_{cat}$ micro-mol/min/mg | $K_M$ mM | $k_{cat}/K_M$ |
|---|---|---|---|
| Linoleic acid | 5.63 | 0.0068 | 828 |
| Arachidonic acid | 0.296 | 0.0175 | 16.9 |
| Linoleyl alcohol | 3.32 | 0.0034 | 982 |
| Methyl linoleate | 1.37 | 0.164 | 8.39 |
| Monolinolein | | | 85.4 |
| 1,3-dilinolein | | | 12.4 |
| Trilinolein | | | 9.15 |

The lipoxygenase showed about twice as high activity toward linolenic acid than linoleic acid at pH 7.

Example 10

Bleaching of β-Carotene by Native Mn-Lipoxygenas

Purified Mn-lipoxygenase was used to bleach beta-carotene at pH 4.5, 6.5 and 9.5. The highest bleaching activity was found at pH 6.5.

Example 11

Effect of LAS on Mn-Lipoxygenase

The activity of *G. graminis* lipoxygenase produced as in Example 4 was measured with LAS up to 400 ppm at pH 7.0 and pH 10. The lipoxygenase was found to be fully stable against LAS up to 400 ppm (the highest concentration tested) at pH 7 and 10. This indicates that the lipoxygenase is stable enough at normal washing conditions, typically pH 10 with 200 ppm of LAS.

---

The invention claimed is:

1. An isolated polypeptide having lipoxygenase activity which:
   a) has at least 98% identity with the mature polypeptide of SEQ ID NO: 2; or
   b) is encoded by the lipoxygenase-encoding part of the DNA sequence cloned into a plasmid present in *Escherichia coil* deposit number DSM 13586.

2. The polypeptide of claim 1, wherein the polypeptide has lipoxygenase activity and is encoded by the lipoxygenase-encoding part of the DNA sequence cloned into a plasmid present in *Escherichia coil* deposit number DSM 13586.

3. A dough composition comprising a polypeptide of claim 1.

4. A detergent composition comprising a polypeptide of claim 1 and a surfactant.

5. The detergent composition of claim 4, wherein the surfactant is an anionic surfactant.

6. The detergent composition of claim 4, wherein the surfactant is a linear alkyl benzenesulfonate.

7. The isolated polypeptide of claim 1, wherein the polypeptide comprises the amino acid sequence of SEQ ID NO:2.

8. The isolated polypeptide of claim 1, wherein the polypeptide consists of the amino acid sequence of SEQ ID NO:2.

9. An isolated polypeptide having lipoxygenase activity which is encoded by the lipoxygenase-encoding part of the DNA sequence cloned into a plasmid present in *Escherichia coli* deposit number DSM 13586.

10. The isolated polypeptide of claim 9, wherein the polypeptide comprises the amino acid sequence of SEQ ID NO:2.

11. The isolated polypeptide of claim 9, wherein the polypeptide consists of the amino acid sequence of SEQ ID NO:2.

12. A dough composition comprising the polypeptide of claim 9.

13. A detergent composition comprising the polypeptide of claim 9 and a surfactant.

* * * * *

SEQUENCE LISTING

<160> NUMBER OF SEQ ID NOS: 31

<210> SEQ ID NO 1
<211> LENGTH: 1857
<212> TYPE: DNA
<213> ORGANISM: Gaeumannomyces graminis
<220> FEATURE:
<221> NAME/KEY: CDS
<222> LOCATION: (1)..(1854)
<220> FEATURE:
<221> NAME/KEY: mat_peptide
<222> LOCATION: (49)..()

<400> SEQUENCE: 1 atg cgc tcc agg atc ctt gcc ata gtc ttc gcg gca cgc cat gtg gca        48

```
                Met Arg Ser Arg Ile Leu Ala Ile Val Phe Ala Ala Arg His Val Ala
                    -15             -10                  -5                  -1 gcg ctg cca ctc gct gcc gaa gac gct gcg gcg acg ctg tct ttg acg         96
Ala Leu Pro Leu Ala Ala Glu Asp Ala Ala Ala Thr Leu Ser Leu Thr
 1           5                  10                  15 tcc agc gcc tcc agc acc acc gtg ctc ccg tct ccg acc cag tac acg        144
Ser Ser Ala Ser Ser Thr Thr Val Leu Pro Ser Pro Thr Gln Tyr Thr
             20                  25                  30 ctg ccc aac aac gac ccc aac cag ggg gca cgc aac gcc agt ata gct        192
Leu Pro Asn Asn Asp Pro Asn Gln Gly Ala Arg Asn Ala Ser Ile Ala
             35                  40                  45 cgg aag cgg gag ttg ttc ctc tac ggc cca tcc act ctc ggg cag acg        240
Arg Lys Arg Glu Leu Phe Leu Tyr Gly Pro Ser Thr Leu Gly Gln Thr
 50                  55                  60 acc ttc tac cct acc gga gag ctg ggg aac aac atc tcg gcc cgc gac        288
Thr Phe Tyr Pro Thr Gly Glu Leu Gly Asn Asn Ile Ser Ala Arg Asp
 65                  70                  75                  80 gtg cta ctt tgg cgc caa gat gcg gcg aac cag acg gca acg gcg tac        336
Val Leu Leu Trp Arg Gln Asp Ala Ala Asn Gln Thr Ala Thr Ala Tyr
                 85                  90                  95 cgc gaa gcc aat gag acg ttt gca gat att acc agc cgt ggc ggt ttc        384
Arg Glu Ala Asn Glu Thr Phe Ala Asp Ile Thr Ser Arg Gly Gly Phe
                100                 105                 110 aaa acg ctc gac gac ttt gcg ctc ctc tac aat ggt cac tgg aag gag        432
Lys Thr Leu Asp Asp Phe Ala Leu Leu Tyr Asn Gly His Trp Lys Glu
         115                 120                 125 tcg gtt ccg gag ggc ata tcg aag ggc atg ttg agc aac tac acc tcg        480
Ser Val Pro Glu Gly Ile Ser Lys Gly Met Leu Ser Asn Tyr Thr Ser
 130                 135                 140 gac ctt ctc ttt tcc atg gag cgg ctg tcc tcc aac cct tac gtc ctc        528
Asp Leu Leu Phe Ser Met Glu Arg Leu Ser Ser Asn Pro Tyr Val Leu
 145                 150                 155                 160 aag cgc ctc cac cca gcc aag gac aaa ctg ccg ttc agc gtc gag agc        576
Lys Arg Leu His Pro Ala Lys Asp Lys Leu Pro Phe Ser Val Glu Ser
                 165                 170                 175 aag gtg gtg aag aag ctg acg gcc acc acg ctt gag gcg ctc cac aag        624
Lys Val Val Lys Lys Leu Thr Ala Thr Thr Leu Glu Ala Leu His Lys
                180                 185                 190 ggc ggc cgc ctg ttc ctc gtg gac cac agc tac cag aag aag tac acc        672
Gly Gly Arg Leu Phe Leu Val Asp His Ser Tyr Gln Lys Lys Tyr Thr
         195                 200                 205 ccc cag cca gga cgg tac gcc gcg gcc tgc cag ggg ctt ttc tac ctg        720
Pro Gln Pro Gly Arg Tyr Ala Ala Ala Cys Gln Gly Leu Phe Tyr Leu
 210                 215                 220 gac gcg cgg tcc aac caa ttc ctg cct ctg gca atc aag acc aac gtg        768
Asp Ala Arg Ser Asn Gln Phe Leu Pro Leu Ala Ile Lys Thr Asn Val
 225                 230                 235                 240 ggg gcg gac ctg acg tac acg ccc ctc gac gac aag aac gac tgg ctg        816
Gly Ala Asp Leu Thr Tyr Thr Pro Leu Asp Asp Lys Asn Asp Trp Leu
                 245                 250                 255 ctg gcc aag atc atg ttc aac aac aac gac ctg ttc tac tcc cag atg        864
Leu Ala Lys Ile Met Phe Asn Asn Asn Asp Leu Phe Tyr Ser Gln Met
                260                 265                 270 tac cac gtg ctc ttc cac acg atc ccc gag atc gtg cac gag gcc gcc        912
Tyr His Val Leu Phe His Thr Ile Pro Glu Ile Val His Glu Ala Ala
         275                 280                 285 ttc cgg acg ctg agc gac agg cac ccg gtc atg ggc gtg ctc aac cgc        960
Phe Arg Thr Leu Ser Asp Arg His Pro Val Met Gly Val Leu Asn Arg
 290                 295                 300
```

```
ctc atg tac cag gcc tac gcc atc cgg ccc gtg ggc ggg gct gtg ctc      1008
Leu Met Tyr Gln Ala Tyr Ala Ile Arg Pro Val Gly Gly Ala Val Leu
305                 310                 315                 320 ttc aac ccc ggc ggg ttc tgg gac caa aac ttt ggc ctg ccc gcc tcg      1056
Phe Asn Pro Gly Gly Phe Trp Asp Gln Asn Phe Gly Leu Pro Ala Ser
                325                 330                 335 gcc gcc atc gac ttc ccc ggc tcc gtg tac gcg cag ggc ggg ggc ggg      1104
Ala Ala Ile Asp Phe Pro Gly Ser Val Tyr Ala Gln Gly Gly Gly Gly
            340                 345                 350 ttc cag gcc ggc tac ctg gag aag gac ctg cgg agc cgg ggg ctg gtc      1152
Phe Gln Ala Gly Tyr Leu Glu Lys Asp Leu Arg Ser Arg Gly Leu Val
        355                 360                 365 ggc gag gac agc ggc ccg cgg ctg ccg cac ttc ccc ttc tac gag gac      1200
Gly Glu Asp Ser Gly Pro Arg Leu Pro His Phe Pro Phe Tyr Glu Asp
370                 375                 380 gcg cac cgc ctg atc ggg gcg atc cgg cgc ttc atg cag gcg ttc gtg      1248
Ala His Arg Leu Ile Gly Ala Ile Arg Arg Phe Met Gln Ala Phe Val
385                 390                 395                 400 gac tcg acg tac ggt gcc gac gac ggc gac gac ggg gcg ctg ctg cgc      1296
Asp Ser Thr Tyr Gly Ala Asp Asp Gly Asp Asp Gly Ala Leu Leu Arg
                405                 410                 415 gac tac gag ctg cag aac tgg atc gcc gag gcc aac ggg ccg gcg cag      1344
Asp Tyr Glu Leu Gln Asn Trp Ile Ala Glu Ala Asn Gly Pro Ala Gln
            420                 425                 430 gtg cgc gac ttc ccc gcg gcg ccg ctg cgg cgg cgc gca cag ctg gtg      1392
Val Arg Asp Phe Pro Ala Ala Pro Leu Arg Arg Arg Ala Gln Leu Val
        435                 440                 445 gac gtg ctg acg cac gtg gcc tgg gtc acg ggc ggg gcg cac cac gtc      1440
Asp Val Leu Thr His Val Ala Trp Val Thr Gly Gly Ala His His Val
450                 455                 460 atg aac cag ggc tcg ccc gtc aag ttc tcg ggg gtg ctg ccg ctg cac      1488
Met Asn Gln Gly Ser Pro Val Lys Phe Ser Gly Val Leu Pro Leu His
465                 470                 475                 480 ccg gcg gcg ctg tac gcg ccc atc ccg acg acc aag ggc gcc acc ggc      1536
Pro Ala Ala Leu Tyr Ala Pro Ile Pro Thr Thr Lys Gly Ala Thr Gly
                485                 490                 495 aac ggg acg agg gcg ggc ctg ctg gcg tgg ctg ccc aac gag cgg cag      1584
Asn Gly Thr Arg Ala Gly Leu Leu Ala Trp Leu Pro Asn Glu Arg Gln
            500                 505                 510 gcc gtg gag cag gtc tcg ctg ctc gcg cgc ttc aac cgt gcg cag gtc      1632
Ala Val Glu Gln Val Ser Leu Leu Ala Arg Phe Asn Arg Ala Gln Val
        515                 520                 525 ggg gac agg aag cag acg gtg cgc gac gcc ttc gcc gcg ccc gac ctg      1680
Gly Asp Arg Lys Gln Thr Val Arg Asp Ala Phe Ala Ala Pro Asp Leu
530                 535                 540 ctg gcc ggc aac ggg ccg ggg tac gcg gcg gcc aac gcg agg ttc gtc      1728
Leu Ala Gly Asn Gly Pro Gly Tyr Ala Ala Ala Asn Ala Arg Phe Val
545                 550                 555                 560 gag gac acg ggc cgt ata agt cgc gag atg gcg ggc aga ggg ttc gac      1776
Glu Asp Thr Gly Arg Ile Ser Arg Glu Met Ala Gly Arg Gly Phe Asp
                565                 570                 575 ggc aag ggc ctc agc cag ggc atg ccg ttc gtc tgg acc gcg ctc aat      1824
Gly Lys Gly Leu Ser Gln Gly Met Pro Phe Val Trp Thr Ala Leu Asn
            580                 585                 590 ccc gcc gtc aac cct ttt ttc cta agc gtc taa                          1857
Pro Ala Val Asn Pro Phe Phe Leu Ser Val
        595                 600

<210> SEQ ID NO 2
<211> LENGTH: 618
```

<212> TYPE: PRT
<213> ORGANISM: Gaeumannomyces graminis

<400> SEQUENCE: 2

```
Met Arg Ser Arg Ile Leu Ala Ile Val Phe Ala Arg His Val Ala
    -15                 -10                 -5                  -1
Ala Leu Pro Leu Ala Ala Glu Asp Ala Ala Thr Leu Ser Leu Thr
1               5                   10                  15
Ser Ser Ala Ser Ser Thr Thr Val Leu Pro Ser Pro Thr Gln Tyr Thr
                20                  25                  30
Leu Pro Asn Asn Asp Pro Asn Gln Gly Ala Arg Asn Ala Ser Ile Ala
            35                  40                  45
Arg Lys Arg Glu Leu Phe Leu Tyr Gly Pro Ser Thr Leu Gly Gln Thr
    50                  55                  60
Thr Phe Tyr Pro Thr Gly Glu Leu Gly Asn Asn Ile Ser Ala Arg Asp
65                  70                  75                  80
Val Leu Leu Trp Arg Gln Asp Ala Ala Asn Gln Thr Ala Thr Ala Tyr
                85                  90                  95
Arg Glu Ala Asn Glu Thr Phe Ala Asp Ile Thr Ser Arg Gly Gly Phe
            100                 105                 110
Lys Thr Leu Asp Asp Phe Ala Leu Leu Tyr Asn Gly His Trp Lys Glu
    115                 120                 125
Ser Val Pro Glu Gly Ile Ser Lys Gly Met Leu Ser Asn Tyr Thr Ser
            130                 135                 140
Asp Leu Leu Phe Ser Met Glu Arg Leu Ser Ser Asn Pro Tyr Val Leu
145                 150                 155                 160
Lys Arg Leu His Pro Ala Lys Asp Lys Leu Pro Phe Ser Val Glu Ser
                165                 170                 175
Lys Val Val Lys Lys Leu Thr Ala Thr Thr Leu Glu Ala Leu His Lys
            180                 185                 190
Gly Gly Arg Leu Phe Leu Val Asp His Ser Tyr Gln Lys Lys Tyr Thr
    195                 200                 205
Pro Gln Pro Gly Arg Tyr Ala Ala Ala Cys Gln Gly Leu Phe Tyr Leu
    210                 215                 220
Asp Ala Arg Ser Asn Gln Phe Leu Pro Leu Ala Ile Lys Thr Asn Val
225                 230                 235                 240
Gly Ala Asp Leu Thr Tyr Thr Pro Leu Asp Asp Lys Asn Asp Trp Leu
                245                 250                 255
Leu Ala Lys Ile Met Phe Asn Asn Asp Leu Phe Tyr Ser Gln Met
            260                 265                 270
Tyr His Val Leu Phe His Thr Ile Pro Glu Ile Val His Glu Ala Ala
    275                 280                 285
Phe Arg Thr Leu Ser Asp Arg His Pro Val Met Gly Val Leu Asn Arg
    290                 295                 300
Leu Met Tyr Gln Ala Tyr Ala Ile Arg Pro Val Gly Ala Val Leu
305                 310                 315                 320
Phe Asn Pro Gly Gly Phe Trp Asp Gln Asn Phe Gly Leu Pro Ala Ser
                325                 330                 335
Ala Ala Ile Asp Phe Pro Gly Ser Val Tyr Ala Gln Gly Gly Gly
            340                 345                 350
Phe Gln Ala Gly Tyr Leu Glu Lys Asp Leu Arg Ser Arg Gly Leu Val
    355                 360                 365
Gly Glu Asp Ser Gly Pro Arg Leu Pro His Phe Pro Phe Tyr Glu Asp
370                 375                 380
```

```
Ala His Arg Leu Ile Gly Ala Ile Arg Arg Phe Met Gln Ala Phe Val
385                 390                 395                 400

Asp Ser Thr Tyr Gly Ala Asp Gly Asp Gly Ala Leu Leu Arg
            405                 410                 415

Asp Tyr Glu Leu Gln Asn Trp Ile Ala Glu Ala Asn Gly Pro Ala Gln
            420                 425                 430

Val Arg Asp Phe Pro Ala Ala Pro Leu Arg Arg Ala Gln Leu Val
        435                 440                 445

Asp Val Leu Thr His Val Ala Trp Val Thr Gly Gly Ala His His Val
        450                 455                 460

Met Asn Gln Gly Ser Pro Val Lys Phe Ser Gly Val Leu Pro Leu His
465                 470                 475                 480

Pro Ala Ala Leu Tyr Ala Pro Ile Pro Thr Thr Lys Gly Ala Thr Gly
                485                 490                 495

Asn Gly Thr Arg Ala Gly Leu Leu Ala Trp Leu Pro Asn Glu Arg Gln
            500                 505                 510

Ala Val Glu Gln Val Ser Leu Leu Ala Arg Phe Asn Arg Ala Gln Val
            515                 520                 525

Gly Asp Arg Lys Gln Thr Val Arg Asp Ala Phe Ala Ala Pro Asp Leu
        530                 535                 540

Leu Ala Gly Asn Gly Pro Gly Tyr Ala Ala Ala Asn Ala Arg Phe Val
545                 550                 555                 560

Glu Asp Thr Gly Arg Ile Ser Arg Glu Met Ala Gly Arg Gly Phe Asp
                565                 570                 575

Gly Lys Gly Leu Ser Gln Gly Met Pro Phe Val Trp Thr Ala Leu Asn
            580                 585                 590

Pro Ala Val Asn Pro Phe Phe Leu Ser Val
            595                 600

<210> SEQ ID NO 3
<211> LENGTH: 1013
<212> TYPE: DNA
<213> ORGANISM: Gaeumannomyces graminis

<400> SEQUENCE: 3
gccctgccga acaacgaccc caaccagggg gcacgcaacg ccagtatagc tcggaagcgg      60
gagttgttcc tctacggccc atccactctc gggcagacga ccttctaccc taccggagag     120
ctggggaaca acatctcggc ccgcgacgtg ctactttggc gccaagatgc ggcgaaccag     180
acggcaacgg cgtaccgcga agccaatgag acgtttgcag atattaccag cgtatgtgct     240
gatcacatct atgcgtgtag tggccagtct gtttaggagg ctgccagttc ttcctttcgc     300
acttggtatt ggtacctacc tacccaccta acctaggtac taacacgtct cgttgggcta     360
tagcgtggcg gtttcaaaac gctcgacgac tttgcgctcc tctacaatgg tcactggaag     420
gagtcggttc cggagggcat atcgaaggg catgttgagca actacacctc ggaccttctc     480
ttttccatgg agcggctgtc ctccaaccct tacgtcctca agcgcctcca cccagccaag     540
gacaaactgc cgttcagcgt cgagagcaag gtggtgaaga agctgacggc caccacgctt     600
gaggcgctcc acaagggcgg ccgcctgttc ctcgtggacc acagctacca gaagaagtgc     660
accccccagc caggacggta cgccgcgcc tgccaggggc ttttctacct ggacgcgcgg     720
tccaaccaat tcctgcctct ggcaatcaag accaacgtgg gggcggacct gacgtacacg     780
cccctcgacg acaagaacga ctggctgctg ccaagatca tgttcaacaa caacgacctg     840
```

```
ttctactccc agatgtacca cgtgctcttc cacacgatcc ccgagatcgt gcacgaggcc    900
gccttccgga cgctgagcga caggcacccg gtcatgggcg tgctcaaccg cctcatgtac    960
caggcctacg ccatccggcc cgtgggcggg gccgtgctct caaccccgg cgg           1013
```

<210> SEQ ID NO 4
<211> LENGTH: 4098
<212> TYPE: DNA
<213> ORGANISM: Gaeumannomyces graminis

<400> SEQUENCE: 4

```
gtcgactcgg cgatgcacgg gccatgtcga attaattcaa ttccatcgag tcctgcacgc     60
actttaggaa gctccaagcc aaggcactat gaaagttcac aatcgggcat ttgactacca    120
cggcgatttg acgccccagc cgagccgaca ggagcctcaa tatcactcat gtgtctgcac    180
atgggcaggc agaccacagc atcccactat ctcttgcgca ccttcttctc acatcagcca    240
aaacactcca ctatcggacc acccgatcag ccctgtacaa atcaaaagaa ccataacaag    300
gtcgctttac caggaatatc cccctcggtg gctgtaagag gttgggtgcc ttgcagagta    360
taagacgttt tgtgttcatgt tcctagtctc ccttttcctcc attcacgctg ccagctgaca    420
ccaagccata tgtctgacta ttcgactgct acactatgcc cattgtgata agcccgcgcc    480
gcttaatacc acggaccata catcgaaaac ctcaacttcc aagtcggtaa atacgttgtc    540
atgtgatggt agaaggatgc ctcgccgttt ggatcaataa actgtcccctt ctgtggtgcg    600 gcccgagacc ccaggattac tcaggctgga taataatatc tagctcctcc cccattattt    660
gtgttacttc aaattcgata gatggatggt tcgggcaccc tcgtcgctgg aatggcgatc    720
tgcagaaaat ccacacagga ggaacagagc tgacatggaa attgtgaagg agtcggcctg    780
tctgatggcg atggcgaaat tatctcaact agatctctcg gtccaacgtc agcctcgtac    840
cagtgatatc gccgtctaca ggtgcctagg aagtactgcg ccccgatcat ccgctgtcac    900
agcttcaatg tttcggtctc gccgacatat attgcccatg aaaacgattc aacgtgaggc    960
ggcaacccag tcaagcttcc tattgtcgcc atgaccggtg caagatgtca ccgcgccggg   1020
cacacgatat ttcttaggca tgccacacac agattgtggc atactagcaa aatctgcctc   1080
tgtttgtgat ccgatggctt gcatcaaaat gcagttcccg tccgtcccgg gctgacagct   1140
ggggtgtcat tggacggatc ggtgcggcca ccacctacta ggtgcgatta ttgatactca   1200
acgtgaccaa taagcccagc aattttttccg aacaccctct cgggcatatc caactggagc   1260 taaggggggcg gcctgtagga ttcctccgtg acctcatgag agctgagaga gctcagctct   1320
cagctcggtt gagcataagc ccgaagcctt gaccgaggct ggaggtgggc gcagtgagac   1380
acccttgagg gccgtgtcct ttagtggcta aaggatagt gagtatttaa aagtcgagga   1440
aaggctgcat cagcaccatc atgatttccc tttacctcta aggcatttgt gcagtagttc   1500
gctcgttgtt tgcttcttag cccggtagac gctcacgacc aaggctccac cttcgctcga   1560
cgaaatgcgc tccaggatcc ttgccatagt cttcgcggca cgccatgtgg cagcgctgcc   1620
actcgctgcc gaagacgctg cggcgacgct gtctttgacg tccagcgcct ccagcaccac   1680
cgtgctcccg tctccgaccc agtacacgct gcccaacaac gaccccaacc aggggggcacg   1740 caacgccagt atagctcgga agcgggagtt gttcctctac ggcccatcca ctctcgggca   1800
gacgaccttc taccctaccg gagagctggg gaacaacatc tcggcccgcg acgtgctact   1860
ttggcgccaa gatgcggcga accagacggc aacggcgtac cgcgaagcca atgagacgtt   1920
tgcagatatt accagcgtat gtgctgatca catctatgcg tgtagtggcc agtctgttta   1980
```

-continued

```
ggaggctgcc agttctttct ttcgcacttg gtattggtac ctacctaccc acctaaccta    2040
ggtactaaca cgtctcgttg ggctatagcg tggcggtttc aaaacgctcg acgactttgc    2100
gctcctctac aatggtcact ggaaggagtc ggttccggag gcatatcga agggcatgtt    2160
gagcaactac acctcggacc ttctcttttc catggagcgg ctgtcctcca acccttacgt    2220
cctcaagcgc ctccacccag ccaaggacaa actgccgttc agcgtcgaga gcaaggtggt    2280
gaagaagctg acggccacca cgcttgaggc gctccacaag ggcggccgcc tgttcctcgt    2340
ggaccacagc taccagaaga agtacacccc ccagccagga cggtacgccg cggcctgcca    2400
ggggcttttc tacctggacg cgcggtccaa ccaattcctg cctctggcaa tcaagaccaa    2460
cgtgggggcg gacctgacgt acacgcccct cgacgacaag aacgactggc tgctggccaa    2520
gatcatgttc aacaacaacg acctgttcta ctcccagatg taccacgtgc tcttccacac    2580
gatccccgag atcgtgcacg aggccgcctt ccggacgctg agcgacaggc acccggtcat    2640
gggcgtgctc aaccgcctca gtaccaggc ctacgccatc cggcccgtgg gcggggctgt    2700
gctcttcaac cccggcgggt tctgggacca aaactttggc ctgcccgcct cggccgccat    2760
cgacttcccc ggctccgtgt acgcgcaggg cggggcgggg ttccaggccg gctacctgga    2820
gaaggacctg cggagccggg ggctggtcgg cgaggacagc ggcccgcggc tgccgcactt    2880
ccccttctac gaggacgcgc accgcctgat cggggcgatc cggcgcttca tgcaggcgtt    2940
cgtggactcg acgtacggtg ccgacgacgg cgacgacggg gcgctgctgc gcgactacga    3000
gctgcagaac tggatcgccg aggccaacgg gccggcgcag gtgcgcgact ccccgcggc    3060
gccgctgcgg cggcgcgcac agctggtgga cgtgctgacg cacgtggcct gggtcacggg    3120
cggggcgcac acgtcatga accagggctc gcccgtcaag ttctcggggg tgctgccgct    3180
gcacccggcg cgcgctgtacg cgccatccc gacgaccaag ggcgccaccg gcaacgggac    3240
gagggcgggc ctgctggcgt ggctgcccaa cgagcggcag gccgtggagc aggtctcgct    3300
gctcgcgcgc ttcaaccgtg cgcaggtcgg ggacaggaag cagacggtgc gcgacgcctt    3360
cgccgcgccc gacctgctgg ccggcaacgg gccggggtac gcggcggcca acgcgaggtt    3420
cgtcgaggac acgggccgta taagtcgcga gatggcgggc agagggttcg acggcaaggg    3480
cctcagccag ggcatgccgt tcgtctggac gcgctcaat cccgccgtca ccctttttt    3540
cctaagcgtc taaaaggcct ggccaaagct cagctaattg tggattcggt gtcaaggcct    3600
gtcgccctcg gcgacctgag acgggagatg gggtttatga agagcgagga tggacattgg    3660
aggtattggg tggtaattaa cagcatgtgg agggagggct acacgagcca aactctgtaa    3720
tggatggcca ccagctgcta gtcagcagtt cccacattcc ccagaatcac ggctaccgaa    3780
tcgaatgttc acagcacccg actttccatg catatgttca tgtcgccggc ctggttgctt    3840
gcatgcatcc acgtgcgtgc ctggccatgc gagccatgcg agcagtagcc ctggcgacgc    3900
caagggggga caaagcaggc agtgatggag gatggtaaca accataatgt actttagtct    3960
ggatgcaagt ccgtggctag ggaggaaaaa ggacgtgtct cgcccgcagg aggtagggcg    4020
cggactttt ggcgaggatg atccacccc gagcttttcc aaatgaagtc atgaccttgg    4080
cataaaatgt gtctcaca                                                  4098
```

<210> SEQ ID NO 5
<211> LENGTH: 575
<212> TYPE: DNA
<213> ORGANISM: Gaeumannomyces graminis -continued

```
<400> SEQUENCE: 5
agacgctcac gaccaaggct ccaccttcgc tcgacgaaat gcgctccagg atccttgcca      60
tagtcttcgc ggcacgccat gtggcagcgc tgccactcgc tgccgaagac gctgcggcga     120
cgctgtcttt gacgtccagc gcctccagca ccaccgtgct cccgtctccg acccagtaca     180
cgctgcccaa caacgacccc aaccaggggg cacgcaacgc cagtatagct cggaagcggg     240
agttgttcct ctacggccca tccactctcg gcagacgac cttctaccct accggagagc      300
tggggaacaa catctcggcc cgcgacgtgc tactttggcg ccaagatgcg gcgaaccaga     360
cggcaacggc gtaccgcgaa gccaatgaga cgtttgcaga tattaccagc cgtggcggtt     420
tcaaaacgct cgacgacttt gcgctcctct acaatggtca ctggaaggag tcggttccgg     480
agggcatatc gaagggcatg ttgagcaact acacctcgga ccttctcttt tccatggagc     540
ggctgtcctc caaccttac gtcctcaagc gcctc                                 575

<210> SEQ ID NO 6
<211> LENGTH: 1611
<212> TYPE: DNA
<213> ORGANISM: Gaeumannomyces graminis

<400> SEQUENCE: 6
cggctgtcct ccaacccctta cgtcctcaag cgcctccacc cagccaagga caaactgccg      60
ttcagcgtcg agagcaaggt ggtgaagaag ctgacggcca ccacgcttga ggcgctccac     120
aagggcggcc gcctgttcct cgtggaccac agctaccaga agaagtacac cccccagcca     180
ggacggtacg ccgcggcctg ccaggggctt ttctacctgg acgcgcggtc caaccaattc     240
ctgcctctgg caatcaagac caacgtgggg cggacctga cgtacacgcc cctcgacgac      300
aagaacgact ggctgctggc caagatcatg ttcaacaaca cgacctgtt ctactcccag      360 atgtaccacg tgctcttcca cacgatcccc gagatcgtgc acgaggccgc cttccggacg     420
ctgagcgaca ggcacccggt catgggcgtg ctcaaccgcc tcatgtacca ggcctacgcc     480
atccggcccg tgggcgggc tgtgctcttc aaccccggcg ggttctggga ccaaaacttt     540
ggcctgcccg cctcggccgc catcgacttc cccggctccg tgtacgcgca gggcggggc      600 gggttccagg ccggctacct ggagaaggac ctgcggagcc gggggctggt cggcgaggac     660
agcggcccgc ggctgccgca cttccccttc tacgaggacg cgcaccgcct gatcggggcg     720
atccggcgct tcatgcaggc gttcgtggac tcgacgtacg gtgccgacga cggcgacgac     780
ggggcgctgc tgcgcgacta cgagctgcag aactggatcg ccgaggccaa cgggccggcg     840
caggtgcgcg acttccccgc ggcgccgctg cggcggcgcg cacagctggt ggacgtgctg     900
acgcacgtgg cctgggtcac gggcggggcg caccacgtca tgaaccaggg ctcgcccgtc     960
aagttctcgg gggtgctgcc gctgcacccg gcggcgctgt acgcgcccat cccgacgacc    1020
aagggcgcca ccgcaacgg gacgagggcg ggcctgctgg cgtggctgcc caacgagcgg    1080
caggccgtgg agcaggtctc gctgctcgcg cgcttcaacc gtgcgcaggt cggggacagg    1140
aagcagacgt gcgcgacgc cttcgccgcg cccgacctgc tggccggcaa cgggccgggg    1200
tacgcggcgg ccaacgcgag gttcgtcgag acacgggcc gtataagtcg cgagatggcg    1260
ggcagagggt tcgacggcaa gggcctcagc cagggcatgc cgttcgtctg gaccgcgctc    1320
aatcccgccg tcaaccctt ttttcctaagc gtctaaaagg cctggccaaa gctcagctaa     1380
ttgtggattc ggtgtcaagg cctgtcgccc tcggcgacct gagacgggag atggggttta    1440
tgaagagcga ggatggacat tggaggtatt gggtggtaat taacagcatg tggagggagg    1500
```

```
gctacacgag ccaaactctg taatggatgg ccaccagctg ctagtcagca gttcccacat    1560
tccccagaat cacggctacc gaatcgaatg ttcacagcaa aaaaaaaaa a              1611

<210> SEQ ID NO 7
<211> LENGTH: 1857
<212> TYPE: DNA
<213> ORGANISM: Gaeumannomyces graminis

<400> SEQUENCE: 7
atgcgctcca ggatccttgc catagtcttc gcggcacgcc atgtggcagc gctgccactc      60
gctgccgaag acgctgcggc gacgctgtct ttgacgtcca gcgcctccag caccaccgtg     120
ctcccgtctc cgacccagta cacgctgccc aacaacgacc ccaaccaggg ggcacgcaac     180
gccagtatag ctcggaagcg ggagttgttc ctctacggcc catccactct cgggcagacg     240
accttctacc ctaccggaga gctggggaac aacatctcgg cccgcgacgt gctactttgg     300
cgccaagatg cggcgaacca gacggcaacg gcgtaccgcg aagccaatga gacgtttgca     360
gatattacca gccgtggcgg tttcaaaacg ctcgacgact ttgcgctcct ctacaatggt     420
cactggaagg agtcggttcc ggagggcata tcgaagggca tgttgagcaa ctacacctcg     480
gaccttctct tttccatgga gcggctgtcc tccaacccct tacgtcctca agcgcctcca     540
ccagccaagg acaaactgcc gttcagcgtc gagagcaagg tggtgaagaa gctgacggcc     600
accacgcttg aggcgctcca caagggcggc cgcctgttcc tcgtggacca cagctaccag     660
aagaagtaca ccccccagcc aggacggtac gccgcgcgcct gccaggggct tttctacctg     720
gacgcgcggt ccaaccaatt cctgcctctg gcaatcaaga ccaacgtggg ggcggacctg     780
acgtacacgc cctcgacga caagaacgac tggctgctgg ccaagatcat gttcaacaac     840
aacgacctgt tctactccca gatgtaccac gtgctcttcc acacgatccc cgagatcgtg     900
cacgaggccg ccttccggac gctgagcgac aggcacccgg tcatgggcgt gctcaaccgc     960
ctcatgtacc aggcctacgc catccggccc gtgggcgggg ctgtgctctt caaccccggc    1020
gggttctggg accaaaactt tggcctgccc gcctcggccg ccatcgactt ccccggctcc    1080
gtgtacgcgc agggcgggg cgggttccag gccggctacc tggagaagga cctgcggagc    1140
cgggggctgg tcggcgagga cagcggcccg cggctgccgc acttcccctt ctacgaggac    1200
gcgcaccgcc tgatcggggc gatccggcgc ttcatgcagg cgttcgtgga ctcgacgtac    1260
ggtgccgacg acggcgacga cggggcgctg ctgcgcgact acgagctgca gaactggatc    1320
gccgaggcca acgggccggc gcaggtgcgc gacttccccg cggcgccgct gcggcggcgc    1380
gcacagctgg tggacgtgct gacgcacgtg gcctgggtca cgggcggggc gcaccacgtc    1440
atgaaccagg gctcgcccgt caagttctcg ggggtgctgc cgctgcaccc ggcggcgctg    1500
tacgcgccca tcccgacgac caagggcgcc accggcaacg ggacgagggc gggcctgctg    1560
gcgtggctgc ccaacgagcg gcaggccgtg gagcaggtct cgctgctcgc gcgcttcaac    1620
cgtgcgcagg tcggggacag gaagcagacg gtgcgcgacg ccttcgccgc gcccgacctg    1680
ctggccggca cgggccgggg gtacgcggcg gccaacgcga ggttcgtcga ggacacgggc    1740
cgtataagtc gcgagatggc gggcagaggg ttcgacggca agggcctcag ccagggcatg    1800
ccgttcgtct ggaccgcgct caatcccgcc gtcaacccct ttttcctaag cgtctaa       1857

<210> SEQ ID NO 8
<211> LENGTH: 216
<212> TYPE: PRT
```

<213> ORGANISM: Gaeumannomyces graminis

<400> SEQUENCE: 8

```
Arg Gly Gly Phe Lys Thr Leu Asp Asp Phe Ala Leu Leu Tyr Asn Gly
1               5                   10                  15

His Trp Lys Glu Ser Val Pro Glu Gly Ile Ser Lys Gly Met Leu Ser
            20                  25                  30

Asn Tyr Thr Ser Asp Leu Leu Phe Ser Met Glu Arg Leu Ser Ser Asn
        35                  40                  45

Pro Tyr Val Leu Lys Arg Leu His Pro Ala Lys Asp Lys Leu Pro Phe
    50                  55                  60

Ser Val Glu Ser Lys Val Val Lys Lys Leu Thr Ala Thr Thr Leu Glu
65                  70                  75                  80

Ala Leu His Lys Gly Gly Arg Leu Phe Leu Val Asp His Ser Tyr Gln
                85                  90                  95

Lys Lys Cys Thr Pro Gln Pro Gly Arg Tyr Ala Ala Ala Cys Gln Gly
            100                 105                 110

Leu Phe Tyr Leu Asp Ala Arg Ser Asn Gln Phe Leu Pro Leu Ala Ile
        115                 120                 125

Lys Thr Asn Val Gly Ala Asp Leu Thr Tyr Thr Pro Leu Asp Asp Lys
    130                 135                 140

Asn Asp Trp Leu Leu Ala Lys Ile Met Phe Asn Asn Asn Asp Leu Phe
145                 150                 155                 160

Tyr Ser Gln Met Tyr His Val Leu Phe His Thr Ile Pro Glu Ile Val
                165                 170                 175

His Glu Ala Ala Phe Arg Thr Leu Ser Asp Arg His Pro Val Met Gly
            180                 185                 190

Val Leu Asn Arg Leu Met Tyr Gln Ala Tyr Ala Ile Arg Pro Val Gly
        195                 200                 205

Gly Ala Val Leu Phe Asn Pro Gly
    210                 215
```

<210> SEQ ID NO 9
<211> LENGTH: 15
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer 1
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: I

<400> SEQUENCE: 9
gccctsccna acaac                                                          15

<210> SEQ ID NO 10
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer 2

<400> SEQUENCE: 10
gcsggsaggc cgaagttctg gtc                                                      23

<210> SEQ ID NO 11
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (3)..(6)
<223> OTHER INFORMATION: I
<220> FEATURE:
<221> NAME/KEY: misc_feature
<222> LOCATION: (3)..(6)
<223> OTHER INFORMATION: I

<400> SEQUENCE: 11
ccnccngggt traasagsac sgcsccscc                                                29

<210> SEQ ID NO 12
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer 4

<400> SEQUENCE: 12
cggctgtcct ccaaccctta cgtcctcaag cgcctc                                        36

<210> SEQ ID NO 13
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer 5

<400> SEQUENCE: 13
gaggcgcttg aggacgtaag ggttggagga cagccg                                        36

<210> SEQ ID NO 14
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer 6
<220> FEATURE:
<221> NAME/KEY: misc_feature
<222> LOCATION: (4)..(9)
<223> OTHER INFORMATION: Bgl II site

<400> SEQUENCE: 14
ggaagatcta tgcgctccag gatccttgcc atagtc                                        36

<210> SEQ ID NO 15
<211> LENGTH: 38
<212> TYPE: DNA
<213> ORGANISM: Artificial Sequence

```
<220> FEATURE:
<223> OTHER INFORMATION: Primer
<220> FEATURE:
<221> NAME/KEY: misc_feature
<223> OTHER INFORMATION: Primer 7
<220> FEATURE:
<221> NAME/KEY: misc_feature
<222> LOCATION: (4)..(9)
<223> OTHER INFORMATION: Xho I site

<400> SEQUENCE: 15
ccgctcgagt tagacgctta ggaaaaaagg gttgacgg                              38

<210> SEQ ID NO 16
<211> LENGTH: 24
<212> TYPE: PRT
<213> ORGANISM: Gaeumannomyces graminis

<400> SEQUENCE: 16

Gly Leu Ser Gln Gly Met Pro Phe Val Trp Thr Ala Leu Asn Pro Ala
1               5                   10                  15

Val Asn Pro Phe Phe Leu Ser Val
            20

<210> SEQ ID NO 17
<211> LENGTH: 27
<212> TYPE: PRT
<213> ORGANISM: Gaeumannomyces graminis

<400> SEQUENCE: 17

Gly Ala Thr Gly Asp Gly Thr Arg Ala Gly Leu Leu Ala Trp Leu Pro
1               5                   10                  15

Asp Glu Arg Gln Ala Val Glu Gln Val Ser Leu
            20                  25

<210> SEQ ID NO 18
<211> LENGTH: 22
<212> TYPE: PRT
<213> ORGANISM: Gaeumannomyces graminis

<400> SEQUENCE: 18

Gly Met Leu Ser Asp Tyr Thr Ser Asp Leu Leu Phe Ser Met Glu Arg
1               5                   10                  15

Leu Ser Ser Asn Pro Tyr
            20

<210> SEQ ID NO 19
<211> LENGTH: 20
<212> TYPE: PRT
<213> ORGANISM: Gaeumannomyces graminis

<400> SEQUENCE: 19

Phe Ser Gly Val Leu Pro Leu His Pro Ala Ala Leu Tyr Ala Pro Ile
1               5                   10                  15

Ile Thr Thr Lys
            20

<210> SEQ ID NO 20
<211> LENGTH: 25
<212> TYPE: PRT
<213> ORGANISM: Gaeumannomyces graminis
<220> FEATURE:
<221> NAME/KEY: misc_feature
<222> LOCATION: (17)..(17)
<223> OTHER INFORMATION: Unknown
```

```
<400> SEQUENCE: 20

Ala Ile Arg Pro Val Gly Gly Ala Val Leu Phe Asn Pro Gly Gly Phe
1               5                   10                  15

Xaa Asp Gln Asn Phe Gly Leu Pro Ala
            20                  25

<210> SEQ ID NO 21
<211> LENGTH: 19
<212> TYPE: PRT
<213> ORGANISM: Gaeumannomyces graminis
<220> FEATURE:
<221> NAME/KEY: misc_feature
<222> LOCATION: (6)..(18)
<223> OTHER INFORMATION: Unknown

<400> SEQUENCE: 21

Ala Leu Pro Asn Asn Xaa Pro Ala Ala Arg Thr Ala Lys Leu His Xaa
1               5                   10                  15

Leu Xaa Leu

<210> SEQ ID NO 22
<211> LENGTH: 1857
<212> TYPE: DNA
<213> ORGANISM: Gaeumannomyces graminis
<220> FEATURE:
<221> NAME/KEY: CDS
<222> LOCATION: (1)..(1854)
<220> FEATURE:
<221> NAME/KEY: mat_peptide
<222> LOCATION: (49)..()

<400> SEQUENCE: 22 atg cgc tcc agg atc ctt gct ata gtc ttc gca gca cgc cat gtg gca      48
Met Arg Ser Arg Ile Leu Ala Ile Val Phe Ala Ala Arg His Val Ala
    -15                 -10                 -5                  -1 gcg ctg cca ctc gct gcc gaa gac gct gcg gcg acg ctg tct ttg acg      96
Ala Leu Pro Leu Ala Ala Glu Asp Ala Ala Ala Thr Leu Ser Leu Thr
1               5                   10                  15 tcc agc gcc tcc agc acc acc gtg ctc ccg tct ccg acc cag tac acg     144
Ser Ser Ala Ser Ser Thr Thr Val Leu Pro Ser Pro Thr Gln Tyr Thr
            20                  25                  30 ctg ccc aac aaa gac ccc aac cag ggg gca cgc aac gcc agt ata gcg     192
Leu Pro Asn Lys Asp Pro Asn Gln Gly Ala Arg Asn Ala Ser Ile Ala
        35                  40                  45 cgg aag cgg gag ttg ttc ctc tac ggc cca tcc acg ctc ggg cag acg     240
Arg Lys Arg Glu Leu Phe Leu Tyr Gly Pro Ser Thr Leu Gly Gln Thr
50                  55                  60 acc ttc tac cct acc gga gag cta ggg aac aat atc tcg gcc cgc gac     288
Thr Phe Tyr Pro Thr Gly Glu Leu Gly Asn Asn Ile Ser Ala Arg Asp
65                  70                  75                  80 gtg ctg ctt tgg cgc caa gat gcg gcg aac cag acg gca acg gcg tac     336
Val Leu Leu Trp Arg Gln Asp Ala Ala Asn Gln Thr Ala Thr Ala Tyr
                85                  90                  95 cgc gaa gcc aat gag acg ttt gca gat att acc agc cgt ggc ggt ttc     384
Arg Glu Ala Asn Glu Thr Phe Ala Asp Ile Thr Ser Arg Gly Gly Phe
            100                 105                 110 aaa acg ctc gac gac ttt gcg ctc ctc tac aat ggt cac tgg aag gag     432
Lys Thr Leu Asp Asp Phe Ala Leu Leu Tyr Asn Gly His Trp Lys Glu
        115                 120                 125 tcg gtt ccg gag ggc ata tcg aag ggc atg ttg agc aac tac acc tcg     480
Ser Val Pro Glu Gly Ile Ser Lys Gly Met Leu Ser Asn Tyr Thr Ser
    130                 135                 140
```

-continued

| | |
|---|---|
| gac ctt ctc ttt tcc atg gag cgg ctg tcc tcc aac cct tac gtc ctc<br>Asp Leu Leu Phe Ser Met Glu Arg Leu Ser Ser Asn Pro Tyr Val Leu<br>145                 150                155               160 | 528 |
| aag cgc ctc cac cca acc aag gac aaa ctg ccg ttc agc gtc gag agc<br>Lys Arg Leu His Pro Thr Lys Asp Lys Leu Pro Phe Ser Val Glu Ser<br>                   165                170               175 | 576 |
| aag gtg gtg aag aag ctg acg gcc acc acg ctt gag gcg ctc cac aag<br>Lys Val Val Lys Lys Leu Thr Ala Thr Thr Leu Glu Ala Leu His Lys<br>180                 185                190 | 624 |
| ggc ggc cgc ctg ttc ctc gtg gac cac agc tac cag aag aag tac acc<br>Gly Gly Arg Leu Phe Leu Val Asp His Ser Tyr Gln Lys Lys Tyr Thr<br>        195                200               205 | 672 |
| ccc cag cca gga cgg tac gcc gcg gcc tgc cag ggg ctt ttc tac ctg<br>Pro Gln Pro Gly Arg Tyr Ala Ala Ala Cys Gln Gly Leu Phe Tyr Leu<br>210                 215                220 | 720 |
| gac gcg cgg tcc aac cag ttc ctg cct ctg gca atc aag acc aac gtg<br>Asp Ala Arg Ser Asn Gln Phe Leu Pro Leu Ala Ile Lys Thr Asn Val<br>225                 230                235               240 | 768 |
| ggg gtg gat ctg acg tac acg ccc ctc gac gac aag gac gac tgg ctg<br>Gly Val Asp Leu Thr Tyr Thr Pro Leu Asp Asp Lys Asp Asp Trp Leu<br>                   245                250               255 | 816 |
| ctg gcc aag atc atg ttc aac aac aac gac ctg ttc tac tcc cag atg<br>Leu Ala Lys Ile Met Phe Asn Asn Asn Asp Leu Phe Tyr Ser Gln Met<br>                 260                265               270 | 864 |
| tac cac gtg ctc ttc cac acg atc ccc gag atc gtg cac gag gcc gcc<br>Tyr His Val Leu Phe His Thr Ile Pro Glu Ile Val His Glu Ala Ala<br>        275                280               285 | 912 |
| ttc cgg acg ctg agc gac agg cac ccg gtc atg ggc gtg ctc aac cgc<br>Phe Arg Thr Leu Ser Asp Arg His Pro Val Met Gly Val Leu Asn Arg<br>290                 295                300 | 960 |
| ctc atg tac cag gcc tac gcc atc cgg ccc gtg ggc ggg gct gtg ctc<br>Leu Met Tyr Gln Ala Tyr Ala Ile Arg Pro Val Gly Gly Ala Val Leu<br>305                 310                315               320 | 1008 |
| ttc aac ccc ggc ggg ttc tgg gac caa aac ttt ggc ctg ccc gcc tcg<br>Phe Asn Pro Gly Gly Phe Trp Asp Gln Asn Phe Gly Leu Pro Ala Ser<br>                   325                330               335 | 1056 |
| gcc gcc atc gac ttc ccc ggc tcc gtg tac gcg cag ggc ggg ggc ggg<br>Ala Ala Ile Asp Phe Pro Gly Ser Val Tyr Ala Gln Gly Gly Gly Gly<br>        340                345               350 | 1104 |
| ttc cag gcc ggc tac ctg gag aag gac ctg cgg agc cgg ggg ctg atc<br>Phe Gln Ala Gly Tyr Leu Glu Lys Asp Leu Arg Ser Arg Gly Leu Ile<br>355                 360                365 | 1152 |
| ggc gag gac agc ggc ccg cgg ctg ccg cac ttc ccc ttc tac gag gac<br>Gly Glu Asp Ser Gly Pro Arg Leu Pro His Phe Pro Phe Tyr Glu Asp<br>370                 375                380 | 1200 |
| gcg cac cgc ctg atc ggg gcg atc cgg cgc ttc atg cag gcg ttc gtg<br>Ala His Arg Leu Ile Gly Ala Ile Arg Arg Phe Met Gln Ala Phe Val<br>385                 390                395               400 | 1248 |
| gac tcg acg tac ggt gcc gac gac ggc gac gac ggg gcg ctg ctg cgc<br>Asp Ser Thr Tyr Gly Ala Asp Asp Gly Asp Asp Gly Ala Leu Leu Arg<br>                   405                410               415 | 1296 |
| gac tat gag cta cag aac tgg atc gcc gag gcc aac ggg ccg gcg cag<br>Asp Tyr Glu Leu Gln Asn Trp Ile Ala Glu Ala Asn Gly Pro Ala Gln<br>                 420                425               430 | 1344 |
| gtg cgc gac ttc ccc gcg gcg ccg ctg cga cgg cgc gcg cag ctg gtg<br>Val Arg Asp Phe Pro Ala Ala Pro Leu Arg Arg Arg Ala Gln Leu Val<br>        435                440               445 | 1392 |
| gac gtg ctg acg cac gtg gcc tgg atc acg ggc ggg gcg cac cac gtc<br>Asp Val Leu Thr His Val Ala Trp Ile Thr Gly Gly Ala His His Val | 1440 |

```
                    450                 455                 460
atg aac cag ggc tcg ccc gtc aag ttc tcg ggg gtg ctg ccg ctg cac      1488
Met Asn Gln Gly Ser Pro Val Lys Phe Ser Gly Val Leu Pro Leu His
465                 470                 475                 480 ccg gcg gcg ctg tac gcg ccc atc ccg acg gcc aag ggc gcc acc ggc      1536
Pro Ala Ala Leu Tyr Ala Pro Ile Pro Thr Ala Lys Gly Ala Thr Gly
                485                 490                 495 aac ggg acg agg gcg ggc ctg ctg gcg tgg ctg ccc aac gag cgg cag      1584
Asn Gly Thr Arg Ala Gly Leu Leu Ala Trp Leu Pro Asn Glu Arg Gln
            500                 505                 510 gcc gtg gag cag gtc tcg ctg ctc gcg cgc ttc aac cgt gcc cag gtc      1632
Ala Val Glu Gln Val Ser Leu Leu Ala Arg Phe Asn Arg Ala Gln Val
        515                 520                 525 ggg gac agg aag cag acg gtg cgc gac gcc ttc gcc gcg ccc gac ctg      1680
Gly Asp Arg Lys Gln Thr Val Arg Asp Ala Phe Ala Ala Pro Asp Leu
    530                 535                 540 ctg gcc ggc aac ggg ccg ggg tac gcg gcg gcc aac gcg agg ttc gtc      1728
Leu Ala Gly Asn Gly Pro Gly Tyr Ala Ala Ala Asn Ala Arg Phe Val
545                 550                 555                 560 gag gac acg ggc cgt ata agt cgc gag att gcg ggc aga ggg ttt gac      1776
Glu Asp Thr Gly Arg Ile Ser Arg Glu Ile Ala Gly Arg Gly Phe Asp
                565                 570                 575 ggc aag ggc ctc agc cag ggc atg ccg ttc gtc tgg acc gcg ctc aat      1824
Gly Lys Gly Leu Ser Gln Gly Met Pro Phe Val Trp Thr Ala Leu Asn
            580                 585                 590 ccc gcc gtc aac cct ttt ttc ctg agc gtc taa                          1857
Pro Ala Val Asn Pro Phe Phe Leu Ser Val
        595                 600

<210> SEQ ID NO 23
<211> LENGTH: 618
<212> TYPE: PRT
<213> ORGANISM: Gaeumannomyces graminis

<400> SEQUENCE: 23

Met Arg Ser Arg Ile Leu Ala Ile Val Phe Ala Ala Arg His Val Ala
    -15                 -10                 -5                  -1

Ala Leu Pro Leu Ala Ala Glu Asp Ala Ala Thr Leu Ser Leu Thr
1               5                   10                  15

Ser Ser Ala Ser Ser Thr Thr Val Leu Pro Ser Pro Thr Gln Tyr Thr
                20                  25                  30

Leu Pro Asn Lys Asp Pro Asn Gln Gly Ala Arg Asn Ala Ser Ile Ala
            35                  40                  45

Arg Lys Arg Glu Leu Phe Leu Tyr Gly Pro Ser Thr Leu Gly Gln Thr
        50                  55                  60

Thr Phe Tyr Pro Thr Gly Glu Leu Gly Asn Asn Ile Ser Ala Arg Asp
65                  70                  75                  80

Val Leu Leu Trp Arg Gln Asp Ala Ala Asn Gln Thr Ala Thr Ala Tyr
                85                  90                  95

Arg Glu Ala Asn Glu Thr Phe Ala Asp Ile Thr Ser Arg Gly Gly Phe
            100                 105                 110

Lys Thr Leu Asp Asp Phe Ala Leu Leu Tyr Asn Gly His Trp Lys Glu
        115                 120                 125

Ser Val Pro Glu Gly Ile Ser Lys Gly Met Leu Ser Asn Tyr Thr Ser
    130                 135                 140

Asp Leu Leu Phe Ser Met Glu Arg Leu Ser Ser Asn Pro Tyr Val Leu
145                 150                 155                 160
```

```
Lys Arg Leu His Pro Thr Lys Asp Lys Leu Pro Phe Ser Val Glu Ser
                165                 170                 175
Lys Val Val Lys Lys Leu Thr Ala Thr Thr Leu Glu Ala Leu His Lys
            180                 185                 190
Gly Gly Arg Leu Phe Leu Val Asp His Ser Tyr Gln Lys Lys Tyr Thr
        195                 200                 205
Pro Gln Pro Gly Arg Tyr Ala Ala Cys Gln Gly Leu Phe Tyr Leu
    210                 215                 220
Asp Ala Arg Ser Asn Gln Phe Leu Pro Leu Ala Ile Lys Thr Asn Val
225                 230                 235                 240
Gly Val Asp Leu Thr Tyr Thr Pro Leu Asp Asp Lys Asp Asp Trp Leu
                245                 250                 255
Leu Ala Lys Ile Met Phe Asn Asn Asn Asp Leu Phe Tyr Ser Gln Met
            260                 265                 270
Tyr His Val Leu Phe His Thr Ile Pro Glu Ile Val His Glu Ala Ala
        275                 280                 285
Phe Arg Thr Leu Ser Asp Arg His Pro Val Met Gly Val Leu Asn Arg
    290                 295                 300
Leu Met Tyr Gln Ala Tyr Ala Ile Arg Pro Val Gly Ala Val Leu
305                 310                 315                 320
Phe Asn Pro Gly Gly Phe Trp Asp Gln Asn Phe Gly Leu Pro Ala Ser
                325                 330                 335
Ala Ala Ile Asp Phe Pro Gly Ser Val Tyr Ala Gln Gly Gly Gly
            340                 345                 350
Phe Gln Ala Gly Tyr Leu Glu Lys Asp Leu Arg Ser Arg Gly Leu Ile
        355                 360                 365
Gly Glu Asp Ser Gly Pro Arg Leu Pro His Phe Pro Phe Tyr Glu Asp
    370                 375                 380
Ala His Arg Leu Ile Gly Ala Ile Arg Arg Phe Met Gln Ala Phe Val
385                 390                 395                 400
Asp Ser Thr Tyr Gly Ala Asp Asp Gly Asp Asp Gly Ala Leu Leu Arg
                405                 410                 415
Asp Tyr Glu Leu Gln Asn Trp Ile Ala Glu Ala Asn Gly Pro Ala Gln
            420                 425                 430
Val Arg Asp Phe Pro Ala Ala Pro Leu Arg Arg Ala Gln Leu Val
        435                 440                 445
Asp Val Leu Thr His Val Ala Trp Ile Thr Gly Gly Ala His His Val
    450                 455                 460
Met Asn Gln Gly Ser Pro Val Lys Phe Ser Gly Val Leu Pro Leu His
465                 470                 475                 480
Pro Ala Ala Leu Tyr Ala Pro Ile Pro Thr Ala Lys Gly Ala Thr Gly
                485                 490                 495
Asn Gly Thr Arg Ala Gly Leu Leu Ala Trp Leu Pro Asn Glu Arg Gln
            500                 505                 510
Ala Val Glu Gln Val Ser Leu Leu Ala Arg Phe Asn Arg Ala Gln Val
        515                 520                 525
Gly Asp Arg Lys Gln Thr Val Arg Asp Ala Phe Ala Ala Pro Asp Leu
    530                 535                 540
Leu Ala Gly Asn Gly Pro Gly Tyr Ala Ala Asn Ala Arg Phe Val
545                 550                 555                 560
Glu Asp Thr Gly Arg Ile Ser Arg Glu Ile Ala Gly Arg Gly Phe Asp
                565                 570                 575
```

Gly Lys Gly Leu Ser Gln Gly Met Pro Phe Val Trp Thr Ala Leu Asn
               580                 585                 590

Pro Ala Val Asn Pro Phe Phe Leu Ser Val
               595                 600

<210> SEQ ID NO 24
<211> LENGTH: 133
<212> TYPE: DNA
<213> ORGANISM: Gaeumannomyces graminis

<400> SEQUENCE: 24
gtatgtgctg atcacatcta tgcgtgtggt gaccggtctg ctttaggagg ctgccagttc     60
tttctttcgc acttggtatt ggtacctacc tacccaccta acctaggtgc taacacgtct    120
cgttgggcta tag                                                       133

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
aaccagttcc tsccsctcgc satcaa                                          26

<210> SEQ ID NO 26
<211> LENGTH: 27
<212> TYPE: DNA
<213> ORGANISM: Artificial Sequence
<220> FEATURE:
<223> OTHER INFORMATION: Primer

<400> SEQUENCE: 26
gtcgaggtag aagaggccct grcavgc                                         27

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
catccsgtsa tgggygtsct baa                                             23

<210> SEQ ID NO 28
<211> LENGTH: 26
<212> TYPE: DNA
<213> ORGANISM: Artificial Sequence
<220> FEATURE:
<223> OTHER INFORMATION: Primer

<400> SEQUENCE: 28
cggttsagga crcccatvac vggrtg                                          26

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
ccgttcagcg tcgagagcaa gg                                              22

```
<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
tctcggggat cgtgtggaag agca                                              24

<210> SEQ ID NO 31
<211> LENGTH: 32
<212> TYPE: DNA
<213> ORGANISM: Artificial Sequence
<220> FEATURE:
<223> OTHER INFORMATION: Primer

<400> SEQUENCE: 31
ttactagtca tatgcgctcc aggatccttg ct                                     32
```